United States Patent
Tedesco et al.

(10) Patent No.: US 9,202,360 B1
(45) Date of Patent: Dec. 1, 2015

(54) METHODS FOR REMOTE ASSISTANCE OF DISABLED PERSONS HAVING AT LEAST TWO REMOTE INDIVIDUALS WHICH RECEIVE DIFFERENT INDICATIONS

(71) Applicant: HandHold Adaptive, LLC, Shelton, CT (US)

(72) Inventors: Daniel E. Tedesco, Shelton, CT (US); Robert C. Tedesco, Trumbull, CT (US); James A. Jorasch, New York, NY (US)

(73) Assignee: HandHold Adaptive, LLC, Shelton, CT (US)

( * ) Notice: Subject to any disclaimer, the term of this patent is extended or adjusted under 35 U.S.C. 154(b) by 69 days.

(21) Appl. No.: 14/177,754

(22) Filed: Feb. 11, 2014

Related U.S. Application Data

(63) Continuation of application No. 13/892,643, filed on May 13, 2013, now Pat. No. 8,669,864, which is a continuation of application No. 12/703,156, filed on Feb. 9, 2010, now Pat. No. 8,441,356.

(60) Provisional application No. 61/152,919, filed on Feb. 16, 2009.

(51) Int. Cl.
*G08B 21/00* (2006.01)
*G08B 21/02* (2006.01)

(52) U.S. Cl.
CPC ..................................... *G08B 21/02* (2013.01)

(58) Field of Classification Search
CPC .............................. A61B 5/0002; G08B 21/02
USPC ...................... 340/573.1, 539.1–539.2, 573.4
See application file for complete search history.

(56) References Cited

U.S. PATENT DOCUMENTS

| | | |
|---|---|---|
| 5,544,651 A | 8/1996 | Wilk |
| 5,596,994 A | 1/1997 | Bro |
| 5,771,001 A | 6/1998 | Cobb |
| 5,778,882 A | 7/1998 | Raymond et al. |
| 6,198,394 B1 | 3/2001 | Jacobsen et al. |
| 6,529,143 B2 | 3/2003 | Mikkola et al. |
| 6,607,484 B2 | 8/2003 | Suzuki et al. |
| 6,662,016 B1 | 12/2003 | Buckham et al. |
| 6,735,479 B2 | 5/2004 | Fabian et al. |
| 6,753,782 B2 | 6/2004 | Power |

(Continued)

OTHER PUBLICATIONS

Author Unknown, "Whssp—iPhone Application," AppStoreHQ, Retrieved: Aug. 23, 2010, 7 pages, http://www.appstorehq.com/whssp-iphone-30220/app.

(Continued)

*Primary Examiner* — Jeffery Hofsass
(74) *Attorney, Agent, or Firm* — Withrow & Terranova, PLLC

(57) ABSTRACT

A mobile terminal is used to assist individuals with disabilities. A mobile terminal such as a "smartphone", tablet or other commercially available wireless handheld device may be loaded with software. The software may be configured to: (i) store criteria for managing communications between a disabled user of the mobile terminal and a remote caregiver and a second remote individual, (ii) determine whether a criterion is satisfied, and if so (iii) initiate a communication from the mobile terminal to the remote caregiver, and (iv) initiate a second alert to the second remote individual via a second alert type. Thus, through this software, the mobile terminal may dynamically facilitate communications with specific remote caregivers based on specific situations that may confront disabled individuals.

20 Claims, 25 Drawing Sheets

(56) References Cited

U.S. PATENT DOCUMENTS

| | | | |
|---|---|---|---|
| 7,038,590 | B2 | 5/2006 | Hoffman et al. |
| 7,139,722 | B2 | 11/2006 | Perrella et al. |
| 7,308,247 | B2 | 12/2007 | Thompson et al. |
| 7,411,510 | B1 | 8/2008 | Nixon |
| 7,447,508 | B1 | 11/2008 | Tendler |
| 7,689,437 | B1 | 3/2010 | Teller et al. |
| 7,766,828 | B2 | 8/2010 | Ishii et al. |
| 2002/0077123 | A1 | 6/2002 | Otsuka et al. |
| 2003/0069752 | A1 | 4/2003 | LeDain et al. |
| 2006/0148488 | A1 | 7/2006 | Syrbe |
| 2007/0032225 | A1 | 2/2007 | Konicek et al. |
| 2008/0018459 | A1 | 1/2008 | Derrick et al. |
| 2008/0033256 | A1 | 2/2008 | Farhan et al. |
| 2008/0082363 | A1 | 4/2008 | Habashi |
| 2008/0166992 | A1 | 7/2008 | Ricordi et al. |
| 2008/0316036 | A1 | 12/2008 | Nixon |

OTHER PUBLICATIONS

Cohen, Peter, "WiFi 'Social networking tool' comes to Macworld Expo," MacWorld, Retrieved: Aug. 23, 2010, 1 page, http://www.macworld.com/article/48636/2005/12/jambo.html.

Krzykowski, Matthaus, "Loopt opens a lead with location-based service on smartphones," VentureBeat, Jun. 15, 2008, 7 pages, http://social.venturebeat.com/2008/06/15/loopt-opens-a-lead-with-location-based-service-on-smartphones/.

Author Unknown, "Introducing 'Close Call' for the iPhone," Polka, Sep. 28, 2008, 4 pages, http://blog.polka.com/?p=170.

Polka, "My Emergency Info," iTunes Preview, Apple Inc., Copyright: 2010, 2 pages, http://itunes.apple.com/app/my-emergency-info/id282737873?mt=8.

Maltais, Michelle, "Appiphilia: Four iPhone apps to use in case of emergency," Los Angeles Times: Technology Section, Nov. 13, 2008, 4 pages, http://latimesblogs.latimes.com/technology/2008/11/iphone-apps-eme.html.

Author Unknown, "Automatically Sends Emergency SMS and Emails," iDistress, iPhone Toolbox, Nov. 30, 2009, 2 pages, http://iphonetoolbox.com/news/automatically-sends-emergency-sms-and-emails/.

Author Unknown, "iDistress," IPAL Review, iPhone Application List, Nov. 17, 2009, 2 pages, http://iphoneapplicationlist.com/2009/12/01/idistress/.

Grifantini, Kristina, "Cell Phones That Listen and Learn," Technology Review, Published by MIT, Jun. 22, 2009, 4 pages, http:/www.technologyreview.com/communications/22907/.

Hesseldahl, Arik, "There's Gold in 'Reality Mining'," Bloomberg Businessweek: Technology Section, Mar. 24, 2008, 2 pages, http://www.businessweek.com/technology/content/mar2008/tc20080323_387127.htm.

Ewing, Jack, "Nokia Aims to Be No. 1 on the Mobile Web," Bloomberg Businessweek: Strategies Section, Oct. 2, 2008, 2 pages, http://www.businessweek.com/magazine/content/08_41/b4103067214737.htm.

Author Unknown, "DynaVox V and Vmax," Dynavox Mayer-Johnson, Jan. 20, 2010, 12 pages, http://www.dynavoxtech.com/download.ashx?FileId=5&DocId=8c7c2e46-69a5-4477-8b68-3a6f72858423.

Non-Final Office Action for U.S. Appl. No. 12/703,156, mailed Oct. 15, 2012, 8 pages.

Non-Final Office Action for U.S. Appl. No. 13/892,643, mailed Sep. 13, 2013, 5 pages.

Notice of Allowance for U.S. Appl. No. 13/892,643, mailed Oct. 30, 2013, 8 pages.

PROFILE ID: P-0001

PROFILE NAME: JIMMY SMITH | | LOADED AS CURRENT PROFILE?: YES

| RULE NO. | TRIGGER 1 | TRIGGER 1 TYPE | TRIGGER 1 SENSOR(S) | | COVERAGE PERIOD | COMM. MEDIUM / MEDIA | COMM. BODY | CAREGIVER NAME(S) | CAREGIVER CONTACT |
|---|---|---|---|---|---|---|---|---|---|
| 1 | "DEE-O" | BEHAVIOR (SPEECH) | INTEGRATED MIC, PERIPHERAL MIC | ○ | ALWAYS | PHONE CALL | "HELLO, THIS IS REMOTE..." | MOM | 555-555-1671 |
| 2 | OUTSIDE "SAFE ZONE" | ENVIRONMENT (LOCATION) | GPS; TRIANGULATION | ○ | MON–FRI 7:30 AM–3:30 PM | EMAIL; PHONE CALL | "JIMMY IS..." | REMOTE HELP CENTER | HELP@REMOT ECARECEN... |
| 3 | HIGH HEART RATE | BIOMETRIC (HEART RATE) | PERIPHERAL RING | ○ | MON, WED, FRI 7:30 AM–9:30 AM | TEXT MESSAGE | "ATTENTION. JIMMY'S HE..." | DR. SMITHSON; MOM; DAD | 555-555-1671; 555-555-9602... |

FIG. 23

METHODS FOR REMOTE ASSISTANCE OF DISABLED PERSONS HAVING AT LEAST TWO REMOTE INDIVIDUALS WHICH RECEIVE DIFFERENT INDICATIONS

RELATED APPLICATIONS

The present application is a continuation of U.S. patent application Ser. No. 13/892,643, filed May 13, 2013, now U.S. Pat. No. 8,669,864. The '643 application is a continuation of U.S. Pat. No. 8,441,356. The '356 patent claims the benefit of and priority to U.S. Provisional Patent Application Ser. No. 61/152,919, filed Feb. 16, 2009. The contents of these applications are hereby incorporated by reference in their entirety.

FIELD OF THE INVENTION

The present application is directed to providing devices, systems and methods for assisting those with disabilities.

BACKGROUND

With a growing population, the number of developmentally disabled children grows. Additionally, the rates at which children have been diagnosed as developmentally disabled, and particularly diagnosed with autism spectrum disorders (ASD), have steadily increased. Individuals with developmental disabilities often have several challenges in common, including but not limited to speech and language impairments, cognitive deficits, social problems, behavioral problems, memory problems, attention deficits, and sensory processing dysfunction. The developmentally disabled population extends beyond those with ASD to include those with Down syndrome, cerebral palsy, Fragile X syndrome, ADD/ADHD, cognitive challenges, and other disabilities. Moreover, various late-onset disorders and conditions often lead to similar challenges (e.g., Alzheimer's disease, Parkinson's disease, dementia, stroke, and brain injury).

The manifestations of such disabilities can vary greatly from individual to individual (particularly in those with ASD, a disorder known for its "spectrum" of neurological impairments). As time goes by, parents, family members, friends and therapists who spend time with such disabled persons develop their own understanding of each disabled individual's unique set of challenges and faculties. Each caregiver may build his or her own set of tactics for managing challenges that confront the disabled individual, whether health issues, emotional swings, or everyday adjustments to new environments and situations. As these circumstances arise in day to day life, the disabled person may greatly benefit from the assistance of specific caregivers that have grown to know and understand the disabled person.

However, as many such disabled individuals enjoy some level of independence, situations may arise during which a caregiver's help may be beneficial, though the caregiver may not be physically present. A need therefore exists to provide disabled persons with dynamic, circumstantially appropriate, targeted assistance from specific caregivers at specific times.

BRIEF DESCRIPTION OF THE DRAWINGS

FIG. 23 illustrates a first example database suitable for use with the present disclosure.

DETAILED DESCRIPTION

Figure 1:
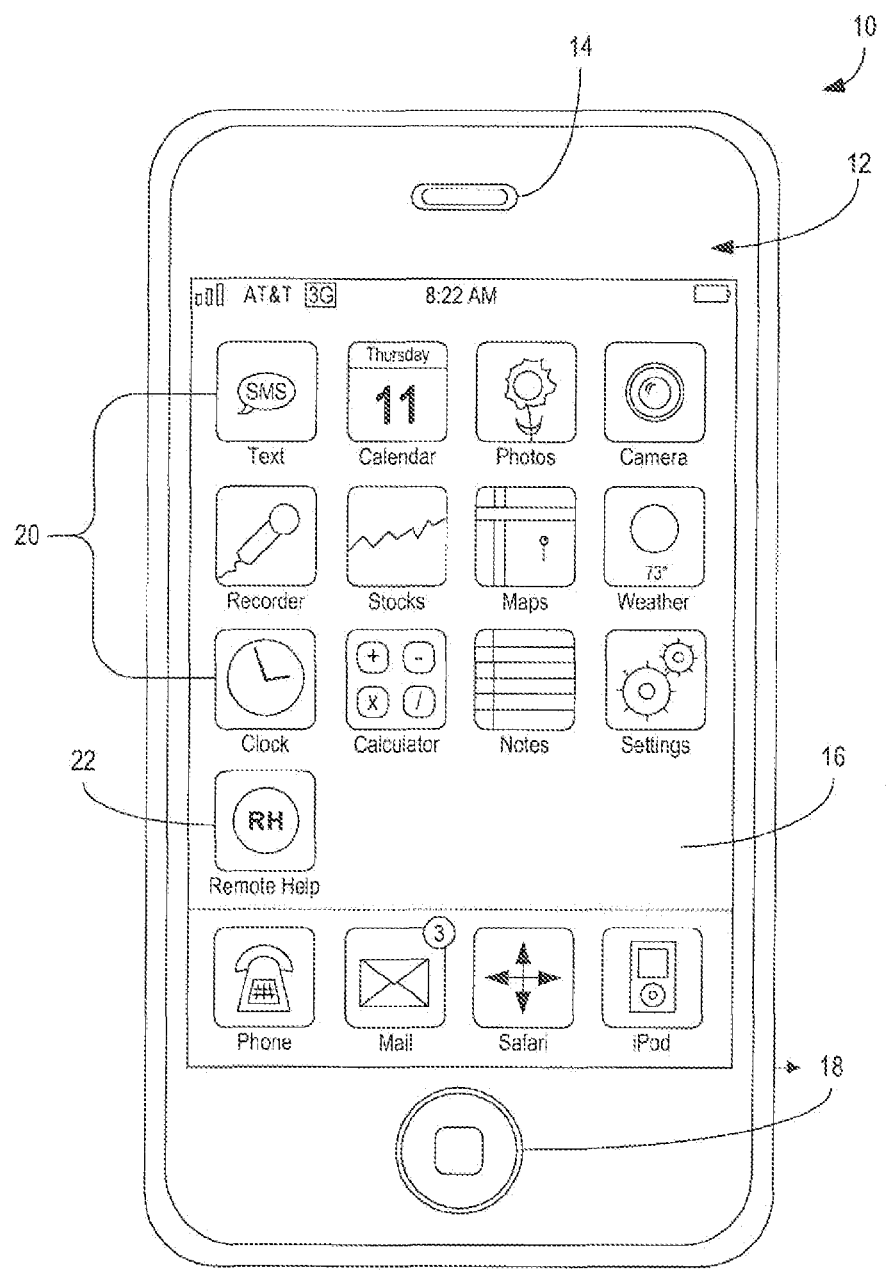
FIG. 1 illustrates a front elevational view of a mobile terminal.

Described herein are methods for assisting individuals with disabilities. In some embodiments, a mobile terminal (e.g., a "smartphone" or other commercially available wireless handheld device described herein) may be loaded with software of the present disclosure. The software may be configured to: (i) store criteria for managing communications between a user of the mobile terminal (e.g., a disabled person) and a remote caregiver, (ii) determine whether a criterion is satisfied, and if so (iii) initiate a communication from the mobile terminal to the remote caregiver, and (iv) receive a response from the remote caregiver. Thus, through software of the present disclosure, the mobile terminal may dynamically facilitate communications with specific remote caregivers based on specific situations that may confront disabled individuals. The mobile terminal may be held by the disabled individual, or a physically present caregiver. The software detects circumstances in which assistance, instructions, guidance, assurance, or information provided by a remote caregiver may be useful, and may in turn automatically initiate communication with a specific remote caregiver.

For example, using (i) the mobile terminal's microphone, (ii) speech recognition technology, and (iii) caregiver-programmed rules stored in memory, the software of the present disclosure may detect that a disabled child is struggling to communicate with another person; specifically, the child is repeatedly producing the utterance "DEE-O", which to most audiences would seem meaningless, though to the child's parent, this utterance is understood as an expression of desire to be "all done". Upon detection of the unknown and/or incomprehensible utterance, a programmed rule instructs the software to contact the parent (e.g., a text message is sent to the parent's mobile phone), informing the parent of the situation. The parent may then, through a line of communication facilitated by the mobile terminal (e.g., a phone call), decipher the child's utterance, and communicate with the child's companions such that the companions or nearby persons may understand the child's the desire to stop the current activity.

In another example, based on data stored or measured by the mobile terminal (i.e., data concerning a disabled person's environment, biology or behavior (including usage of the mobile terminal)) and a programmed rule for reacting to such data, the software may determine that there is a high probability of a medical emergency in association with a disabled child using the mobile terminal. For example, a peripheral heart rate monitor communicating wirelessly with the mobile terminal detects a sudden increase in beats per minute, while simultaneously a microphone detects crying, and a schedule stored within the software indicates the child is a few minutes past a scheduled dose of medication. Based on such criteria, software of the present disclosure may trigger a call to a 24-hour monitoring center, allowing a representative to remotely access the child's medical history, and accordingly provide care instructions via the mobile terminal.

An overview of some of the hardware elements is provided before addressing some of the methods and potential screen configurations associated with embodiments of the present disclosure. A mobile terminal 10 is illustrated in FIG. 1. An exemplary suitable mobile terminal 10 may be the APPLE® IPHONE™ (or IPOD™) and may include a user interface 12 that includes a speaker 14, a microphone 26 (FIG. 2), a touch screen display 16, and a command entry button 18. One or more icons 20 may be displayed on the touch screen display 16. The user may enter commands by touching an icon on the touch screen display 16 or by using the command entry button 18 as is well understood. One such icon 22 may launch software that effectuates embodiments of the present disclosure. While the IPHONE™ is particularly contemplated, the disclosure is not so limited, and any readily portable handheld computing device may be appropriate including personal digital assistants, cellular telephones, WINDOWS MOBILE™ enabled devices, or the like. Further examples of such mobile terminals include, but are not limited to: the BLACKBERRY™ line of wireless devices manufactured by Research in Motion of Waterloo, Ontario, Calif.; the T-MOBILE G1™ or other mobile terminals compatible with the ANDROID operating system as developed by Google, Inc. of Mountain View, Calif.; the PRADA™ or other mobile terminals manufactured by LG ELECTRONICS MOBILECOMM U.S.A, INC. of San Diego, Calif.; the INSTINCT™ or other mobile terminals manufactured by SAMSUNG TELECOMMUNICATIONS AMERICA, LLC; the XPERIA™ X1 or other mobile terminals manufactured by SONY ERICSSON MOBILE COMMUNICATIONS AB of Sweden; the N96 or other mobile terminals manufactured by NOKIA GROUP of Finland; and the PRE™ or other mobile terminals manufactured by PALM, INC. of Sunnyvale, Calif. In other embodiments, a mobile terminal may comprise a portable personal computer with a sufficiently large, touch-sensitive screen (i.e., a "tablet" or "tablet computer" such as the IPAD™ by APPLE®).

Figure 2:
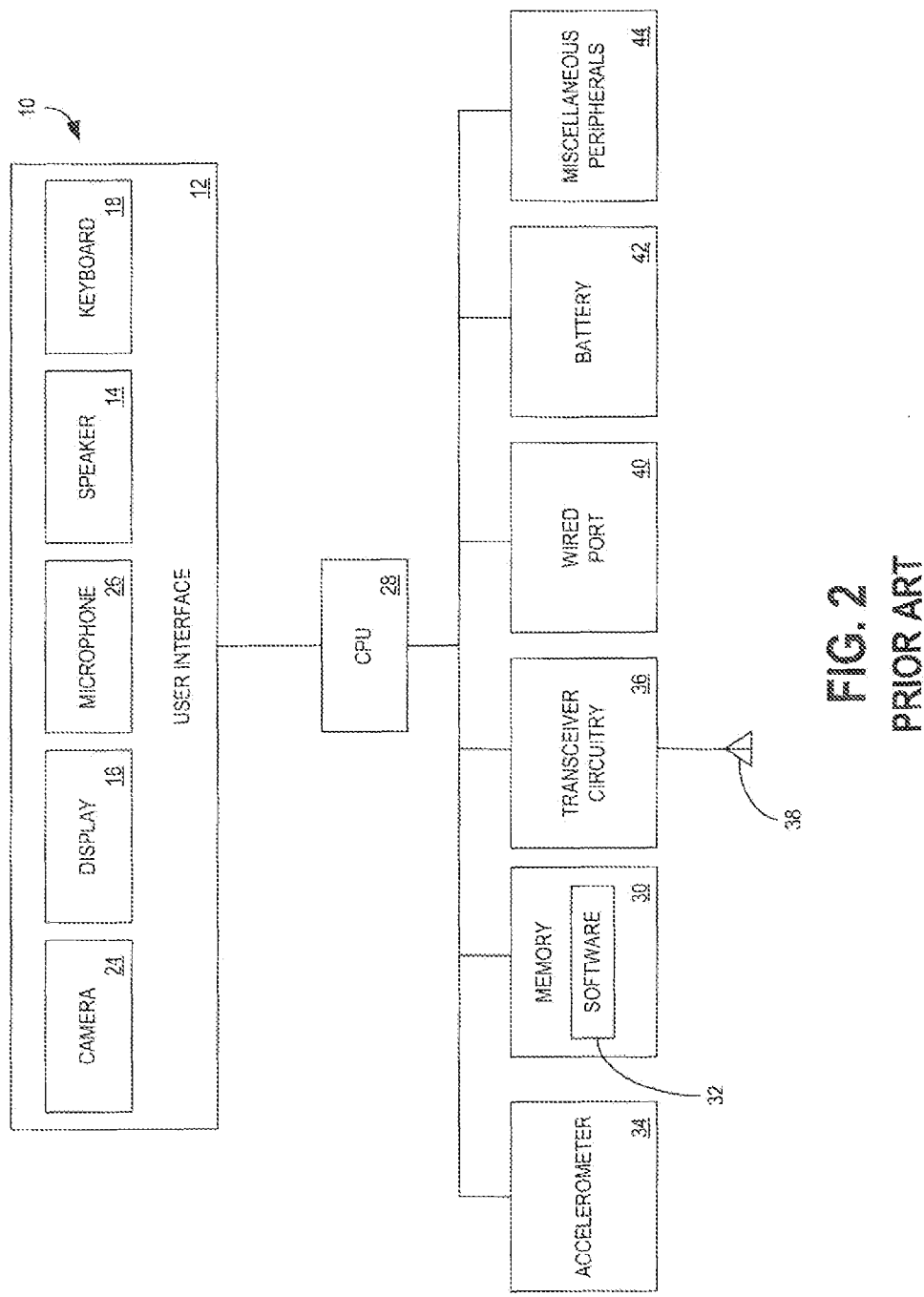
FIG. 2 illustrates a block diagram of the components of a conventional mobile terminal.

A block diagram of the mobile terminal 10 is illustrated in FIG. 2. The mobile terminal 10 includes the elements already illustrated and further includes, within the user interface 12, a camera 24 and the aforementioned microphone 26. The user interface 12 is operatively coupled to a central processor (CPU) 28. The CPU 28 is also operatively coupled to memory 30 with software 32 stored therein, an accelerometer 34, transceiver circuitry 36, which in turn is coupled to an antenna 38, one or more wired ports 40, a battery 42, and any other miscellaneous peripherals 44 as is common in the mobile terminal art (e.g., an internal clock, a vibration unit, a Global Positioning System (GPS) receiver, a thermometer, a light sensor, a proximity sensor, an altimeter, pressure sensor or the like). Any such miscellaneous peripherals 44 may alternately or additionally be embodied as separate peripheral devices in communication with mobile terminal 10 (rather than as a component thereof). The CPU 28 as operated under the instructions of the software is a control system as that term is defined in the Rules of Interpretation & General Definitions set forth below. It should be understood that the hardware configuration depicted by FIG. 2 is illustrative and that mobile terminal 10 may comprise other types of hardware, either as components of the terminal itself, or as peripheral devices in communication with the mobile terminal. Such separate peripheral devices are discussed further below with respect to FIG. 4.

Figure 3:
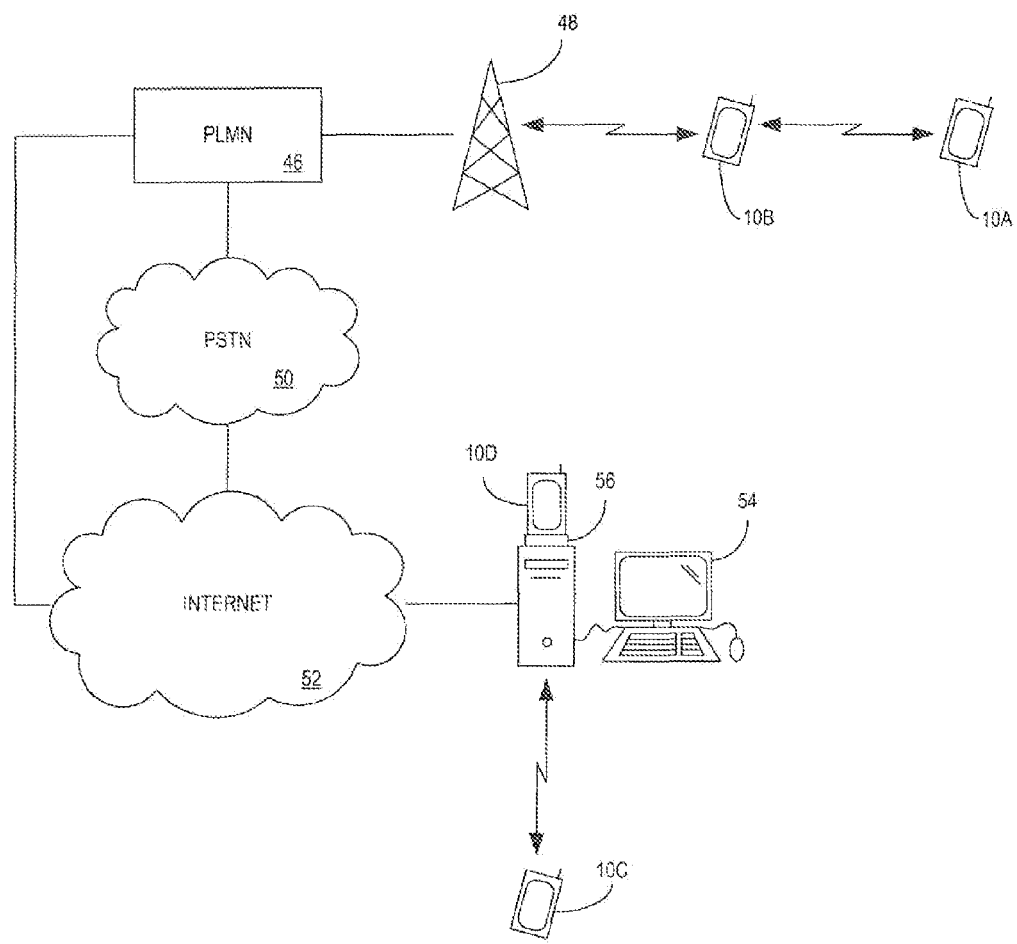
FIG. 3 illustrates a variety of networks in which a mobile terminal may operate.

FIG. 3 illustrates a variety of networks through which mobile terminals 10 may communicate. For example, a first mobile terminal 10A may communicate with a second mobile terminal 10B through a local wireless network/protocol such as a BLUETOOTH™, infrared, or other short range communication protocol. Additionally, or alternatively, the second mobile terminal 10B may communicate with a cellular network such as the Public Land Mobile Network (PLMN) 46 through a cellular base station 48. The PLMN 46 may communicate with the Public Switched Telephone Network (PSTN) 50 and/or the Internet 52. One or more computers 54 may be communicatively coupled to the Internet 52 and may include a wireless transceiver to communicate wirelessly with a third mobile terminal 10C or a docking station 56 to communicate via a wired line with a fourth mobile terminal 10D. More information on networks and communication protocols can be found in the Rules of Interpretation and General Definitions set forth below. Suffice to say that the particular network or communication protocol is not central to embodiments of the present disclosure. Additionally, it should be understood that such protocols may enable communications between mobile terminals and various peripheral devices, including sensors, cameras, microphones, and the like.

Figure 4:
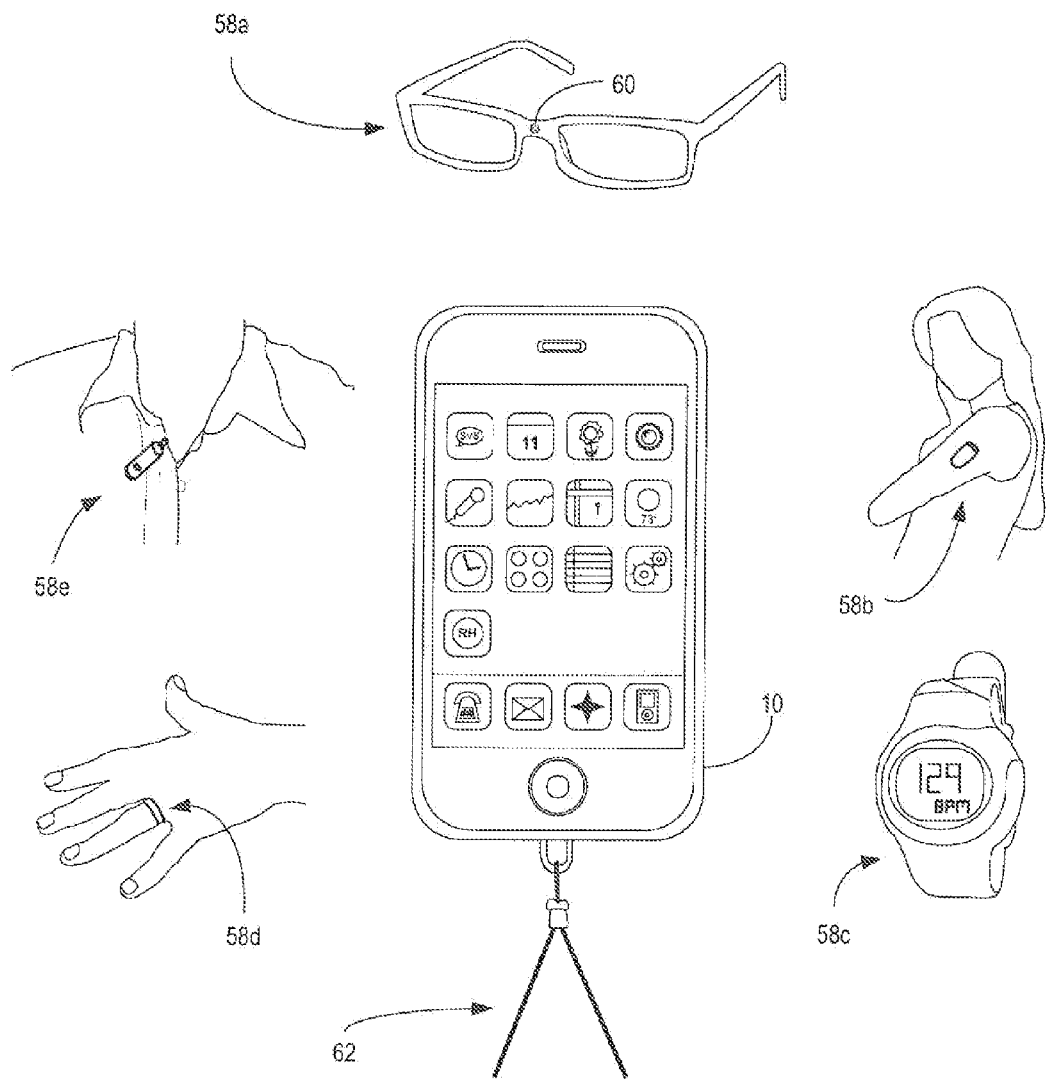
FIG. 4 illustrates various devices which may interface with a mobile terminal.

FIG. 4 illustrates an assortment of such peripheral devices 58a-e, which act as a form of sensor for the reporting to the control system. While other devices may communicate with the mobile terminal 10 as described in this disclosure, a few are specifically shown. An application programming interface (API) may enable interaction between software of the present disclosure and such separate devices. Communication methods which may be utilized between the peripheral devices and the mobile terminal 10 include wireless protocols referenced above (e.g., BLUETOOTH™, infrared), radio frequency identification (RFID), WiFi, and hard wiring (e.g., a cable running from the peripheral device to the mobile terminal 10).

Peripheral eyeglasses 58a may communicate with the mobile terminal 10, and may comprise an optical camera 60, a RFID transponder (not shown), and/or an infrared transmitter (not shown). Eyeglasses 58a may be used to provide information related to (i) the environment surrounding an individual wearing the eyeglasses (e.g., still images or video are taken from outward-facing optical camera 60 and transmitted to mobile terminal 10 through eyeglasses 58a), (ii) pupil dilation of the individual wearing the glasses (e.g., optical-camera 60 is oriented inward to directly monitor the user's eyes), or (iii) the direction of the individual's gaze with respect to the mobile terminal (e.g., the orientation of eyeglasses 58a relative to mobile terminal 10 is determined using RFID, and thus the orientation of the individual's gaze relative to mobile terminal 10 may be inferred). As an example of eye-tracking technology used in conjunction with a mobile terminal, the 3D Eyetracking UI as developed by TAT THE ASTONISHING TRIBE, AB of Sweden for the T-MOBILE G1 mobile terminal alters the user-interface presented by the mobile terminal's display screen based on the orientation of the device to the user's eyes.

Peripheral skin patch 58b may comprise (i) a sensor enabling the measurement of biological properties, and (ii) a transmitter enabling wireless communication with mobile terminal 10. Biological properties measured by skin patch 58b may include temperature, blood glucose (the GUARDIAN® REAL-Time Continuous Glucose Monitoring System, as produced by MEDTRONIC MINIMED, INC. of Northridge, Calif., comprises a sensor embedded within a skin patch that monitors blood sugar levels and a transmitter to send data wirelessly to a receiver via BLUETOOTH™), blood pressure, Galvanic Skin Response (GSR) or electrodermal skin response, heart rate, and cardiac electrical activity (e.g., a wireless ECG patch such as the one developed by the IMEC research center in Belgium). Thus, a user of mobile terminal 10 may also wear skin patch 58b such that biological measurements may be taken in a continuous, periodic, or otherwise specified manner.

Wristwatch 58c may measure and transmit biological data in a manner similar to that of skin patch 58b. Thus, a user of mobile terminal 10 who enjoys wearing a watch may at the same time provide a variety of biological data used by the software of the present disclosure. A variety of commercially available digital wristwatches comprise sensors for measuring such data (e.g., the IRONMAN® Heart Rate Monitor Watch by TIMEX®). In an alternate embodiment, wristwatch 58c may instead take the form of a basic wristband or arm band (i.e., comprising a sensor and transmitter but no clock or stopwatch functionality).

Ring 58d may also measure and transmit biological data in a manner similar to that of skin patch 58b. The ring and its components (e.g., sensors, electronics) may be fashioned from a variety of metals, plastics, composites, and/or semiconductors. In one embodiment, a commercially available ring, such as the MYBEAT Heart Rate Ring by LIFESPAN FITNESS, may be adapted for use with software of the present disclosure.

In another embodiment, a pedometer (not shown) may transmit data to the mobile terminal 10. For example, the Nike+iPod Sport Sport Kit may be employed to track rate of movement (e.g., so that a pace above or below a certain threshold may be considered alone or in combination with other data points to be indicative of a potential situation for the user; for example a pace over a certain threshold may indicate that the user is fleeing a dangerous or frightful situation).

Lapel microphone 58e may be used to receive audio data and re-transmit it to the mobile terminal 10. Thus, a user of mobile terminal 10 may act and speak naturally, with the user's speech transmitted automatically to mobile terminal 10. In one embodiment (not shown), a microphone and speaker may both exist as part of a wireless headset worn by a user of mobile terminal 10 (e.g., affixed via an ergonomic piece of plastic so as to rest around a user's ear). Wireless microphones and headsets are widely available in the commercial marketplace and well known in the mobile terminal art.

In one embodiment (not shown), a biosensor may be permanently affixed to or implanted beneath the user's skin. For example, a subcutaneous electrochemical sensor may be used to continuously measure and report on blood (or interstitial fluid) glucose level. An example of a device employing such a semi-permanent sensor is the FREESTYLE NAVIGATOR® Continuous Glucose Monitoring System by ABBOTT LABORATORIES of Abbott Park, Ill.

Worth discussing at this point is the manner in which mobile terminal 10 may be carried or held. In various embodiments, a mobile terminal 10 may be carried or held by a disabled individual and/or a physically present caregiver. At times, mobile terminal 10 may be carried by hand, but this may not always be desirable, convenient, or possible. While the above described peripheral devices may allow for the placement of mobile terminal 10 inside of a pocket or a purse, some embodiments (e.g., those requiring substantially continuous use of components integrated within mobile terminal 10 itself) may benefit from the placement of mobile terminal 10 outside of a pocket or a purse. In one embodiment, as depicted in FIG. 4, a lanyard 62 may be attached to mobile terminal 10 (or, attached to an after-market case designed to protect the mobile terminal from wear and tear), such that mobile terminal 10 may hang from the neck of an individual, rather than be held by hand, within a pocket or within in a purse. Other cases (not shown) that fasten mobile terminal 10 to the body or clothing may be used, including arm bands, wrist bands, belt clips, and the like. Still further cases (also not shown) may affix mobile terminal 10 to wheelchair arms, head pointers, or other physical devices used to afford the disabled with mobility or the ability to communicate.

In some embodiments, a user of the mobile terminal 10 may be reminded or encouraged to appropriately position the mobile terminal 10 or any associated peripheral devices on or around his or her person. For example, in some embodiments, placement of the mobile terminal 10 around the neck of a disabled user through the use of lanyard 62 may be desirable. Thus, if the mobile terminal's integrated light sensor detects lack of light for a prolonged period of time during a specified coverage period (e.g., suggesting that the device may be in the user's pocket or purse), a vibration unit, speaker 14, or other output device may be actuated to alert the user and encourage him or her to appropriately position the mobile terminal 10 (e.g., the mobile terminal vibrates, and the speaker outputs a ringtone or other alarm). An accelerometer 34 and/or light sensor may then detect that the device has been picked up, at which point instructions for effectively positioning the device may be output (e.g., the display screen 16 outputs a graphical indication of the device hung around a neck, while speaker 14 outputs an audio instruction to "Hang around your neck, please!"). Placement of the mobile terminal 10 or associated peripheral devices in other locations may be encouraged in a similar manner.

It should be noted that in some embodiments encouragement may not be necessary to ensure that the disabled individual carries mobile terminal 10. For example, where mobile terminal 10 is configured to provide "voice output" functionality to assist the disabled user in communicating, the disabled user indeed may depend on mobile terminal 10, and may thus naturally carry the device on his or her person in a manner that facilitates the embodiments of the present disclosure.

Figure 5:
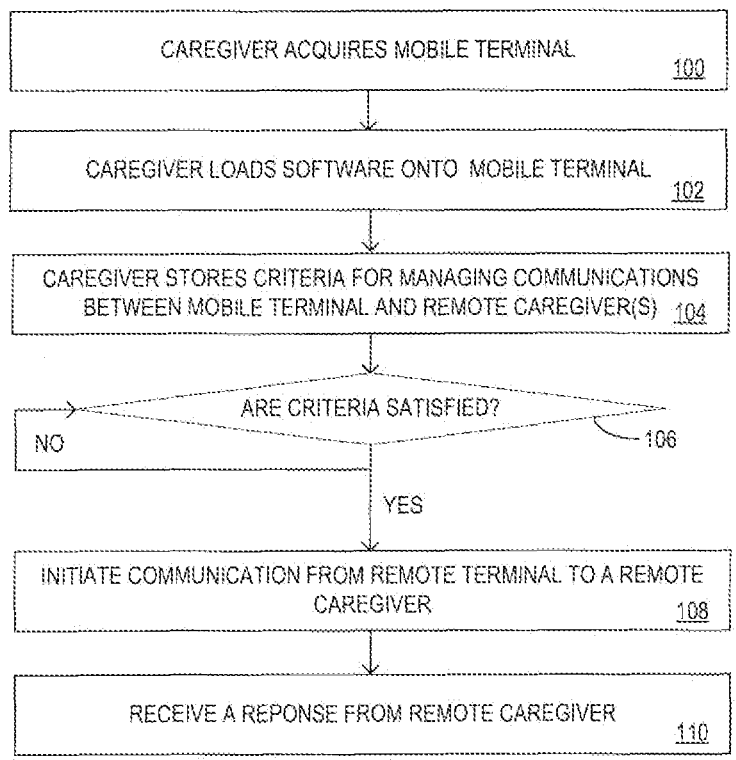
FIG. 5 illustrates a first flow chart showing an exemplary embodiment of the present disclosure.

Against this backdrop of hardware, an overview of an exemplary method is presented starting with reference to FIG. 5 as a flow diagram interspersed with additional Figures for supporting explanatory and exemplary screen shots. Initially, a user acquires a mobile terminal 10 (block 100). This acquisition may be a gift, a purchase, a lease, borrowing, or otherwise. For example, the disabled individual may purchase the mobile terminal 10 and loan it to the caregiver for the purposes of carrying out embodiments of the present disclosure. Alternatively, the caregiver may purchase the mobile terminal 10 for use by and/or with the disabled individual. The caregiver may load the software embodying the present disclosure onto the mobile terminal 10 (block 102). If the mobile terminal 10 has a disk drive or other data storage device or functionality (e.g. flash memory), the software may be loaded from a disk or other source. Otherwise, the software may be loaded onto a computer 54 (e.g., via disk transfer or download) and transferred to the mobile terminal 10 through the docking station 56 or wirelessly. As still another alternative, the mobile terminal 10 may download the software through the PLMN 46 or other technique as desired. The software could be preloaded on the mobile terminal 10 such that when the lease or purchase is made, the software is immediately accessible. The software itself may be free, paid or subsidized in whole or part by a third party (such as a school district or other governmental agency, an insurance company or a private foundation). Note that while it is contemplated that the caregiver performs these and other steps, it is also possible that the disabled individual performs these and the other steps.

Toward the ultimate goal of establishing criteria for managing communications between the mobile terminal 10 and one or more remote caregivers, the caregiver may then configure and store elements of the software, so as to customize the software on behalf of a disabled individual (block 104).

Figure 6:
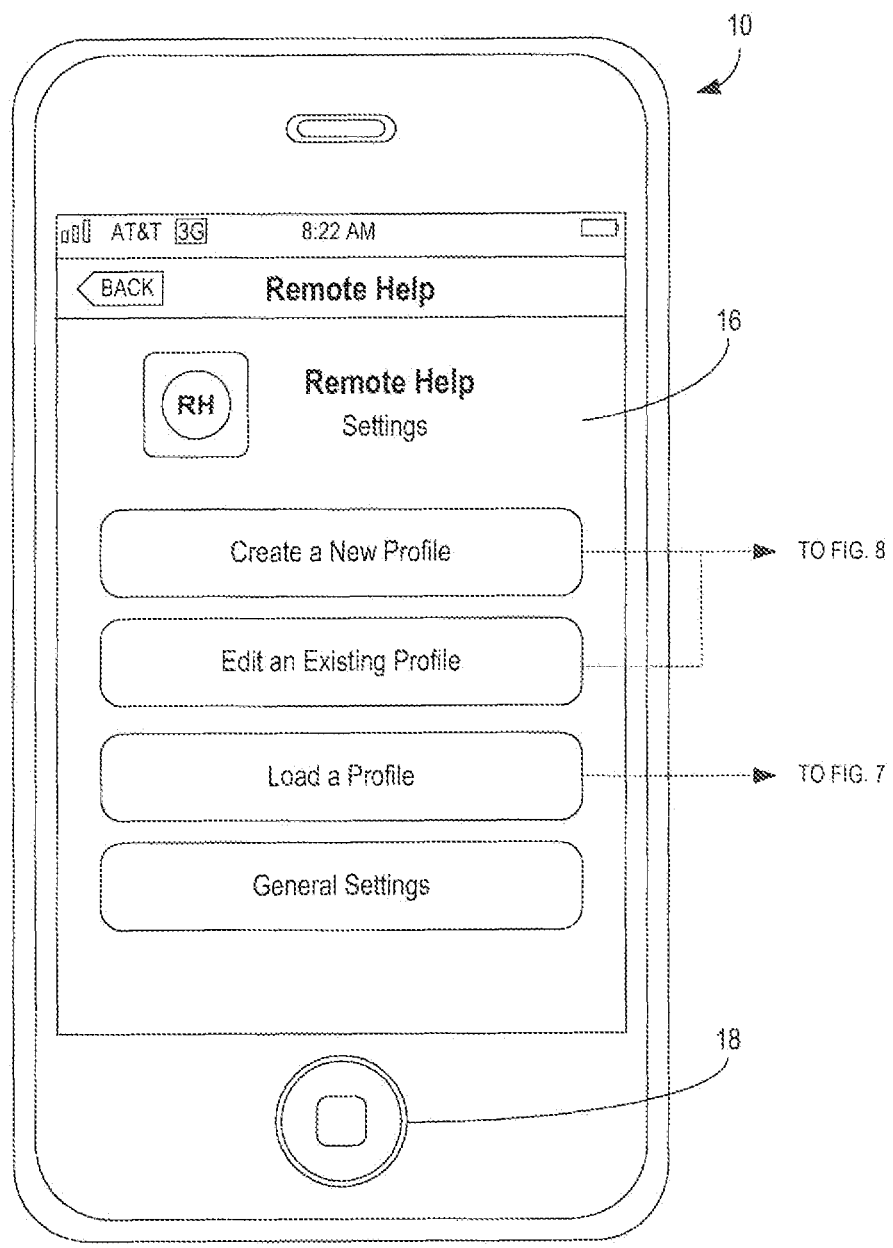
FIG. 6 illustrates a first screen shot associated with the flow chart of FIG. 5.

An exemplary process of configuring and storing the criteria for managing communications between the mobile terminal 10 and the remote caregiver is set forth with reference to the flow chart of FIG. 24. In one scenario, the caregiver may use the mobile terminal 10 to configure the software, such as by selecting a "Settings" icon from a group of icons 20 displayed by the mobile terminal 10, or by selecting a "Settings" option within the software of the present disclosure (block 150). Alternately, computer 54 may be used to configure software settings, which may then be transmitted to a mobile terminal 10 using methodologies described above. In either case, a screen such as that illustrated in FIG. 6 (or one with comparable functionality) may be presented allowing the user to begin customizing the software program. As shown, the caregiver may select from options including "Create a New Profile" (block 152), "Edit an Existing Profile" (block 154), "Load a Profile" (block 156), and "General Settings".

Figure 7:
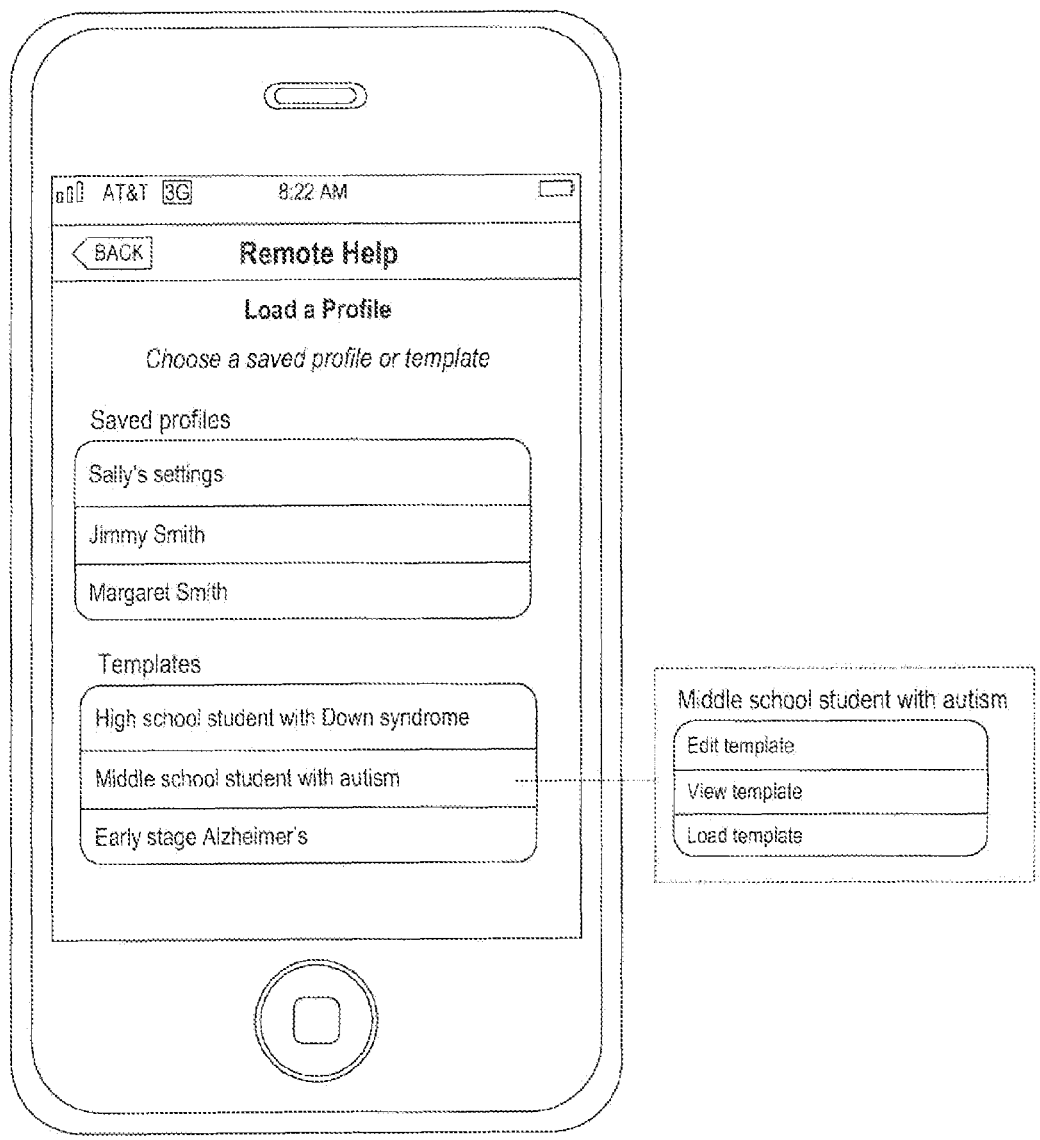
FIG. 7 illustrates a second screen shot associated with the flow chart of FIG. 5.

Continuing the example and assuming the caregiver selects the "Load a Profile" option, a caregiver may select a profile from a list of one or more saved profiles (if available), as shown by the example screen shot of FIG. 7 or from a screen having comparable functionality. Profiles may include those already customized and saved by caregivers for use with particular disabled persons (block 158), or template profiles created as a starting point for serving those with particular disabilities (e.g., settings for someone with early-stage Alzheimer's, settings for a high school student with Down syndrome, etc.) (block 160). Selection of a template may provide an additional menu asking the user if they want to edit the template (block 162), view the template (block 164), or load the template (block 166). If the user selects editing the template, the user may be routed to a screen as if they had selected an option such as the "Edit an Existing Profile" (block 154) choice illustrated by FIG. 6. If the user views the template (block 164), the user may then back out to the "select template" (block 160) using a back command or the user may edit the template (block 162). If the user loads the template at block 166, the user may concurrently view the template after loading and may also edit the template (block 162) through use of the appropriate commands.

If the user selects a saved profile (block 158), the profile is loaded (block 168) and the control system begins to monitor for occurrence of criteria (block 170) as explained in greater detail below. At this point, the process returns to block 106 of FIG. 5.

Figure 8:
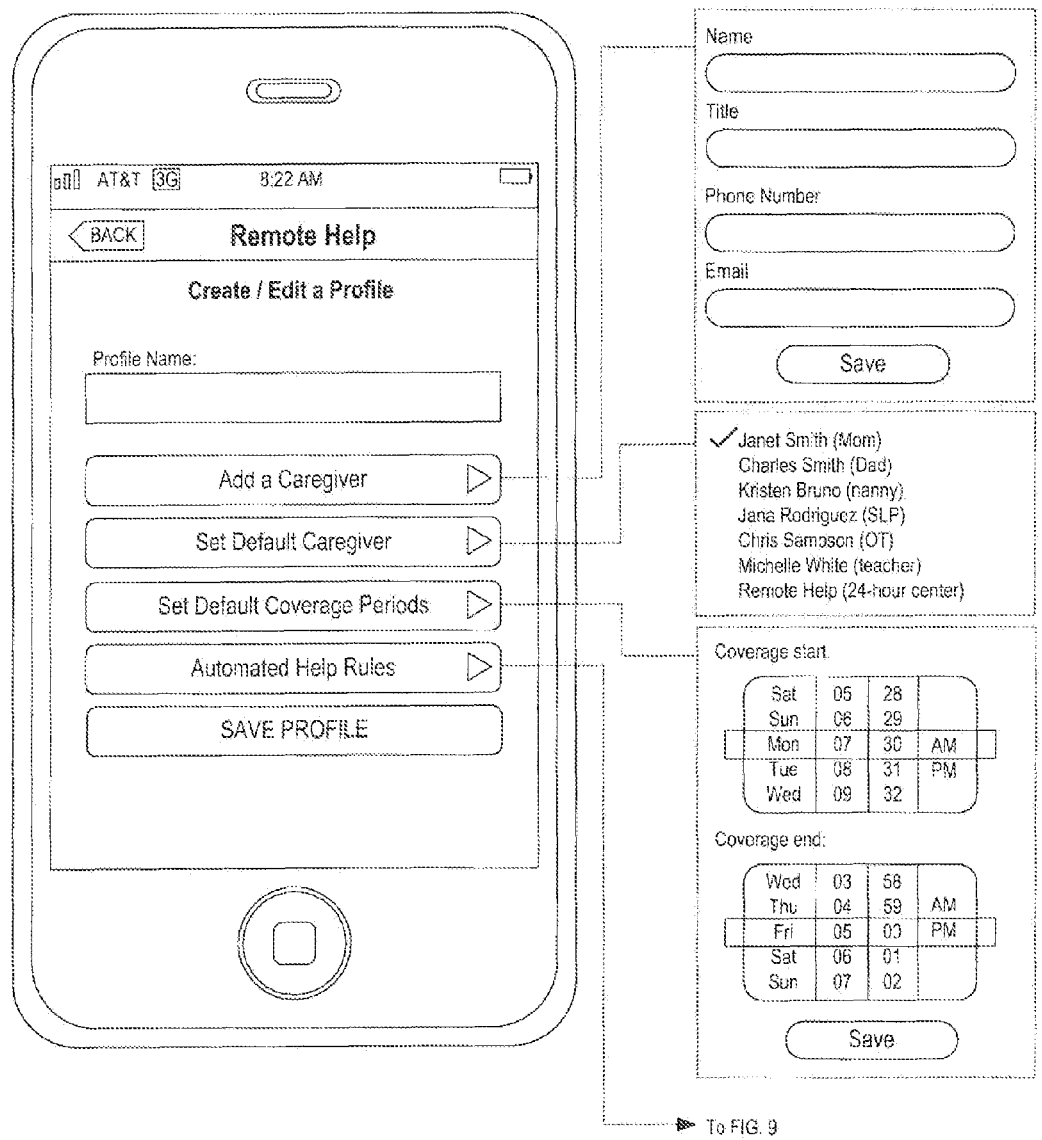
FIG. 8 illustrates a third screen shot associated with the flow chart of FIG. 5.
Figure 24:
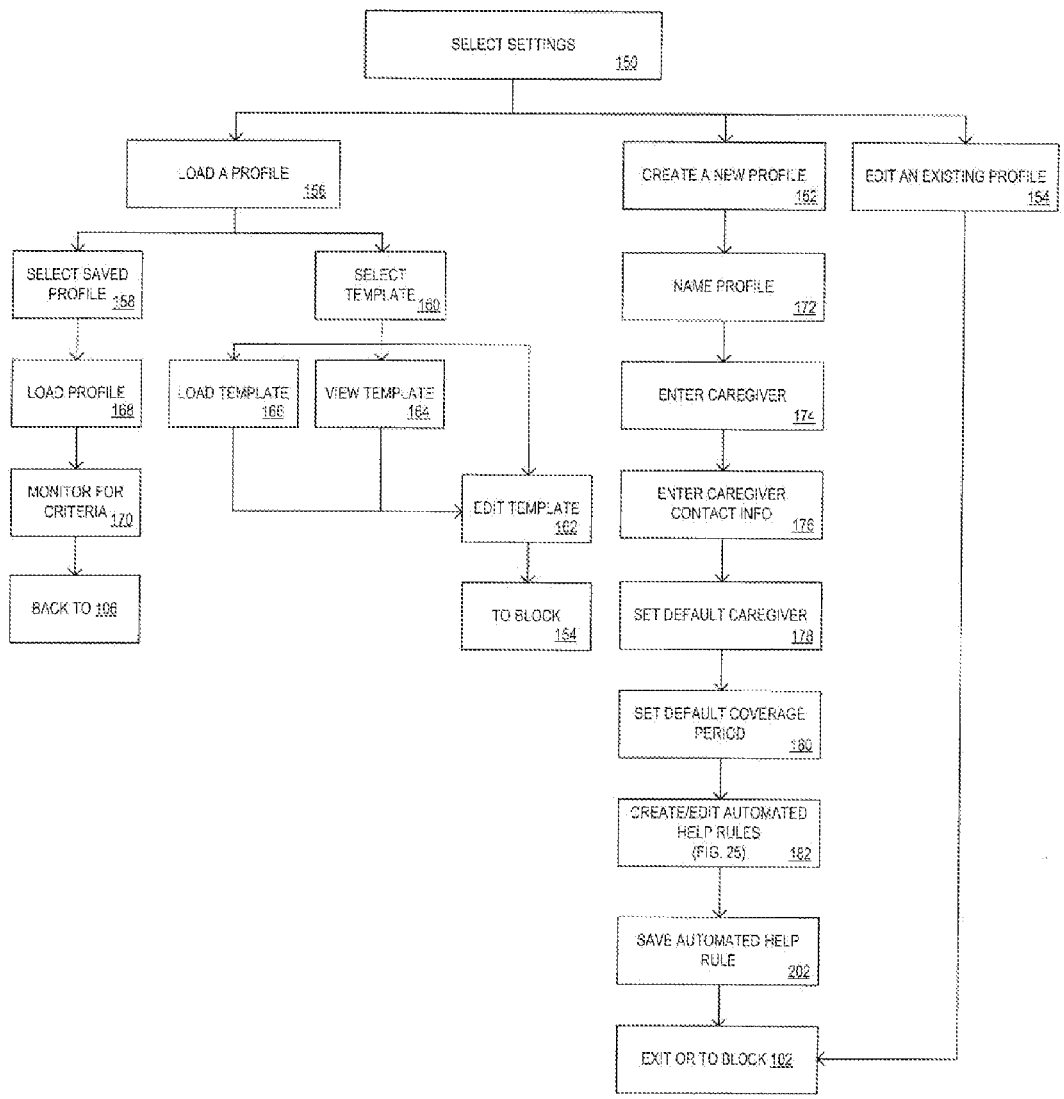
FIGS. 24-25 illustrate an exemplary flow chart outlining an exemplary profile creation process of the present disclosure.

Continuing the example of FIG. 24, and instead assuming the caregiver selects the "Create a New Profile" option (block 152), a screen such as that illustrated by FIG. 8 (or one with comparable functionality) may be presented. This screen allows the caregiver to input and save various types of configuration data in association with a profile, though some software configurations may be pre-programmed or set to "default" values before the caregiver begins this step. Multiple profiles may be created for one or more disabled individuals (e.g., separate profile names of "Jimmy's Remote Help" and "Sally's Remote Help"), allowing for use of the mobile terminal 10 by different individuals at different times if so desired. The caregiver may utilize a keyboard feature (either hard-wired keys or a virtual keyboard, as with the IPHONE™) to enter such a profile name (block 172). For each profile, the caregiver may also: (i) add a remote caregiver (block 174) (e.g., as shown by FIG. 8, the caregiver enters a name, title, phone number, email address, or other contact information (block 176), such as a username for SKYPE™ or another VoIP provider, a username for an instant messaging service, etc.), (ii) set a default remote caregiver (block 178) (e.g., such that if a specific remote caregiver is not listed with respect to a particular automated help rule as described below, the default caregiver may be contacted), (iii) set a default coverage period (block 180) (e.g., such that if a specific time and date are not listed with respect to an automated help rule as described below, default time and date settings may apply to all rules), and (iv) create or edit automated help rules (block 182) (i.e., instructions to automatically initiate communication between the mobile terminal 10 and a remote caregiver based on the satisfaction of specified criteria).

Figure 9:
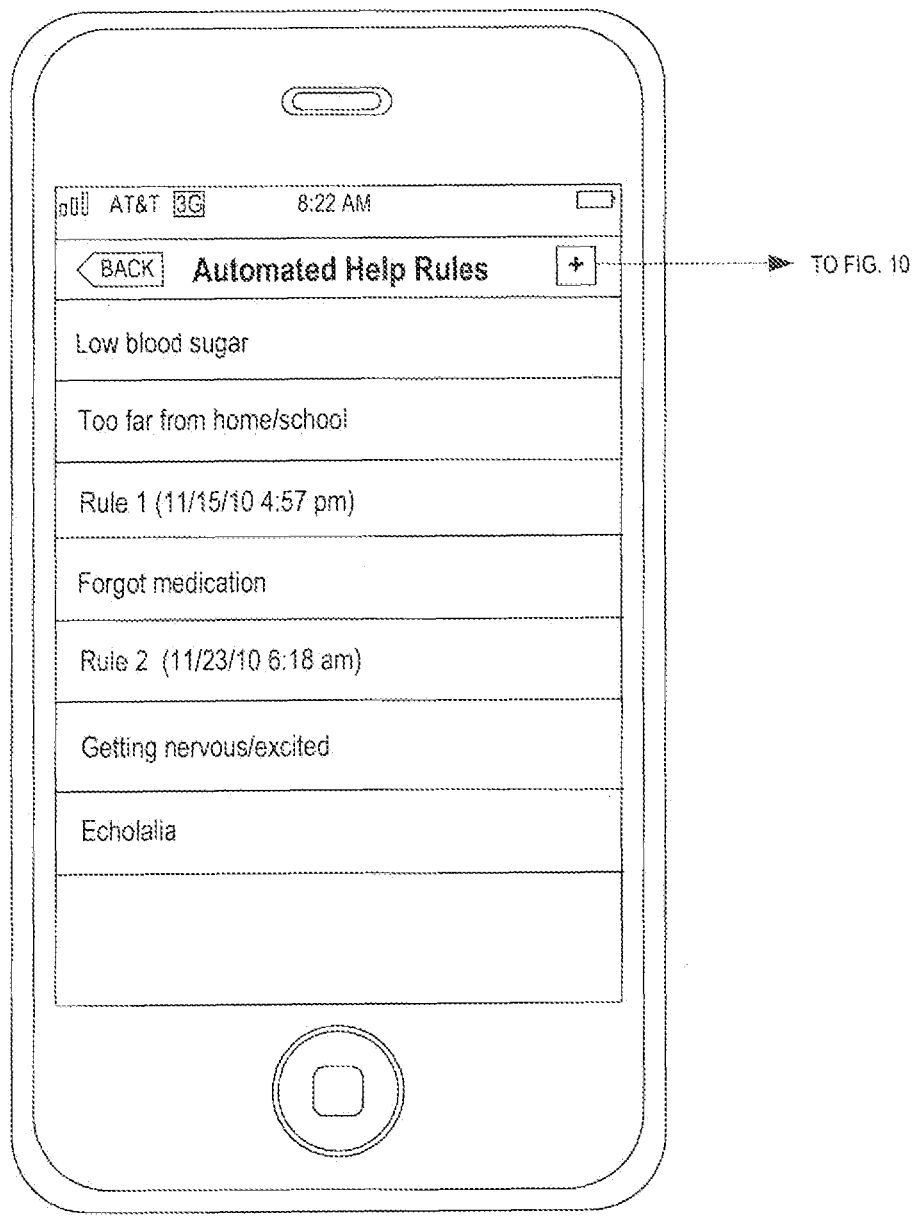
FIG. 9 illustrates a fourth screen shot associated with the flow chart of FIG. 5.
Figure 25:
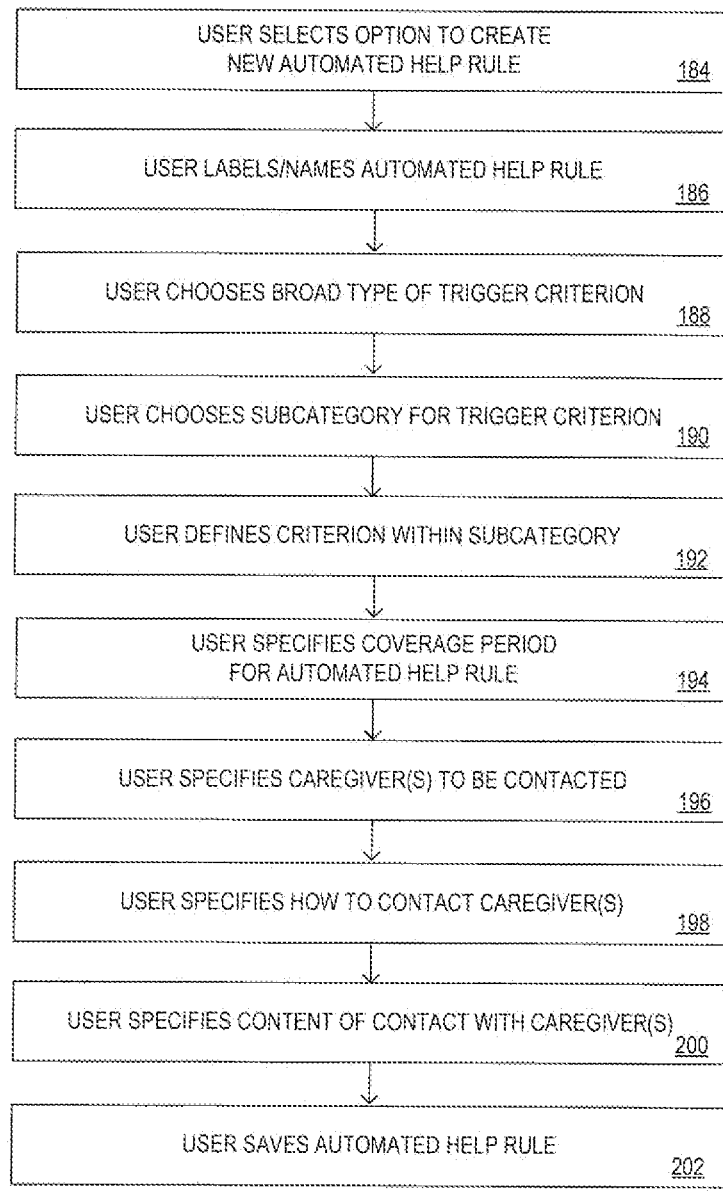

If the user selects the "Automated Help Rules" option illustrated by FIG. 8, the user may be brought to a screen similar in appearance or function to that of FIG. 9. An assortment of programmed rules are shown, including "Low blood sugar" (e.g., created by a caregiver so as to send an alert when a disabled user's blood glucose level falls beneath a threshold), "Rule 1 (11/15/10 4:57 pm)" (e.g., a rule set by a caregiver but not expressly labeled, and so automatically given a label based on the time and date at which it was created), and "Echolalia" (e.g., created by a caregiver so as to automatically open a line of communications with a child with autism who is exhibiting echolalic speech patterns as may be detected by voice recognition software picking up on repetitive speech). The rules shown are examples of those that may be created by caregivers. It is possible that the screen of FIG. 9 may instead show (i) no rules (i.e., a caregiver has yet to create any); (ii) categories of rules (i.e., such that users may organize rules by type); or (iii) template rules (e.g., pre-packed rules bundled as part of the software). Reference is made to FIG. 25, which sets forth a flow chart illustrating an exemplary method for creating a new rule. To continue the example, it is assumed that the user selects the "+" option shown at the top-right of the screen, so as to create a new rule (block 184).

Figure 10:
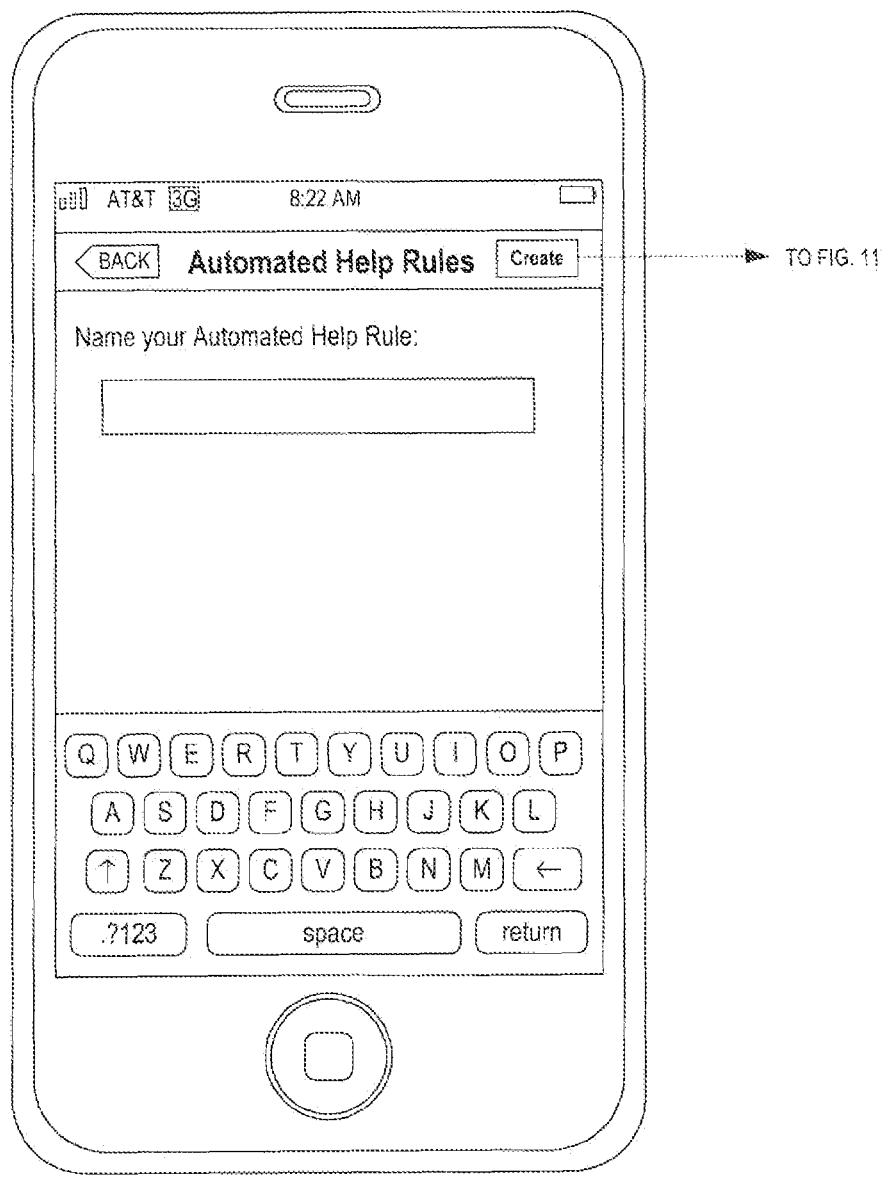
FIG. 10 illustrates a fifth screen shot associated with the flow chart of FIG. 5.

FIG. 10 illustrates a first example screen for configuring a new automated help rule, in which the user is given the option to label the rule (block 186). If the user chooses not to exercise this option and simply presses "Create," a label may be supplied as described above. It should be noted that while a screen such as that shown in FIG. 10 are contemplated, screens with similar functionality may be used without departing from the scope of the present disclosure.

Figure 11:
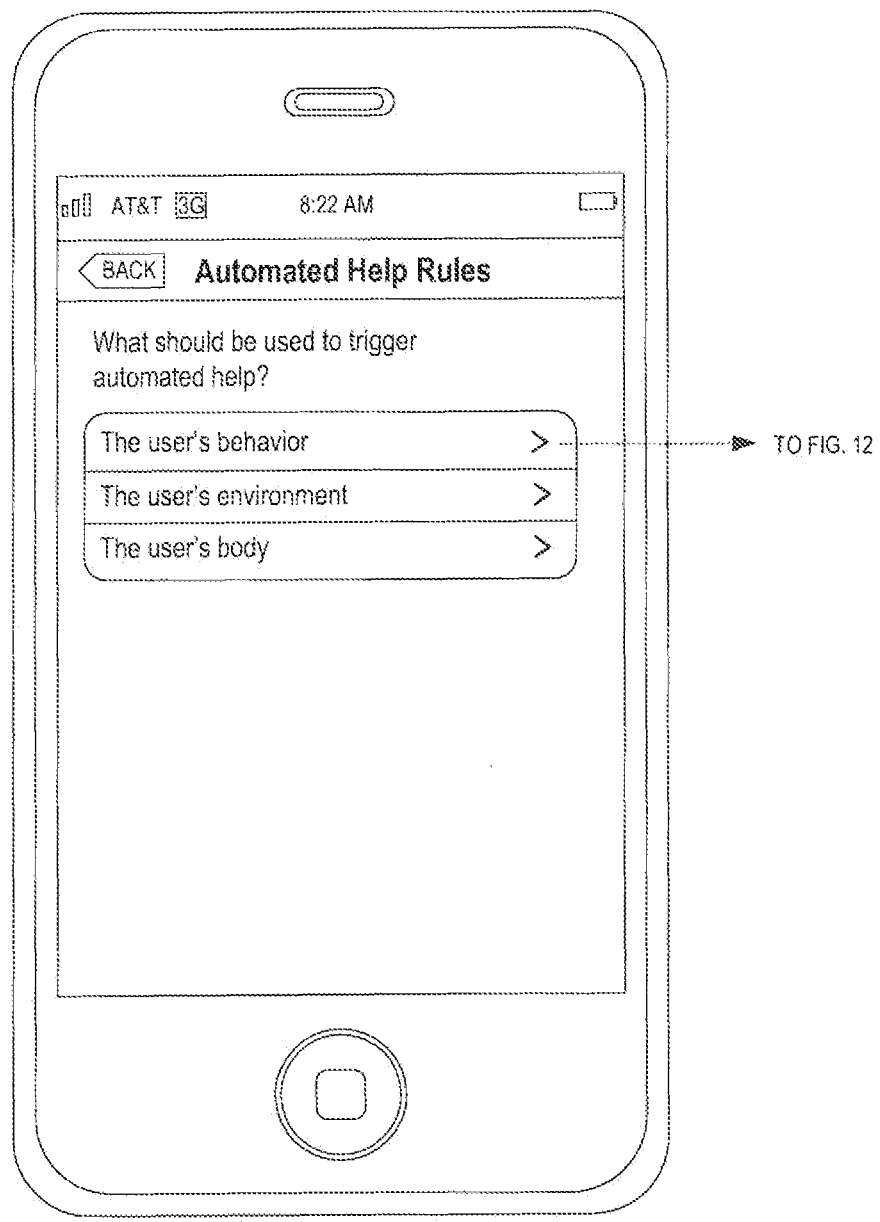
FIG. 11 illustrates a sixth screen shot associated with the flow chart of FIG. 5.

Once the user selects "Create," a second example screen for configuring an automated help rule may be presented, an example of which is shown by FIG. 11. Using a screen such as this or one with comparable functionality, the user may first choose a broad type of criterion ("trigger") (block 188) to be further considered (at block 106 of the flowchart of FIG. 5, as described below) in establishing automated communications between a user of the mobile terminal 10 and a remote caregiver. Three categories of criteria are presented (though others may be used): those based on the user's behavior, those based on the user's environment, and those based on the user's body (i.e., changes in biological or physiological state). Thus, changes in the user's behavior, environment or body may trigger automated communications as specified further in this disclosure.

Figure 12:
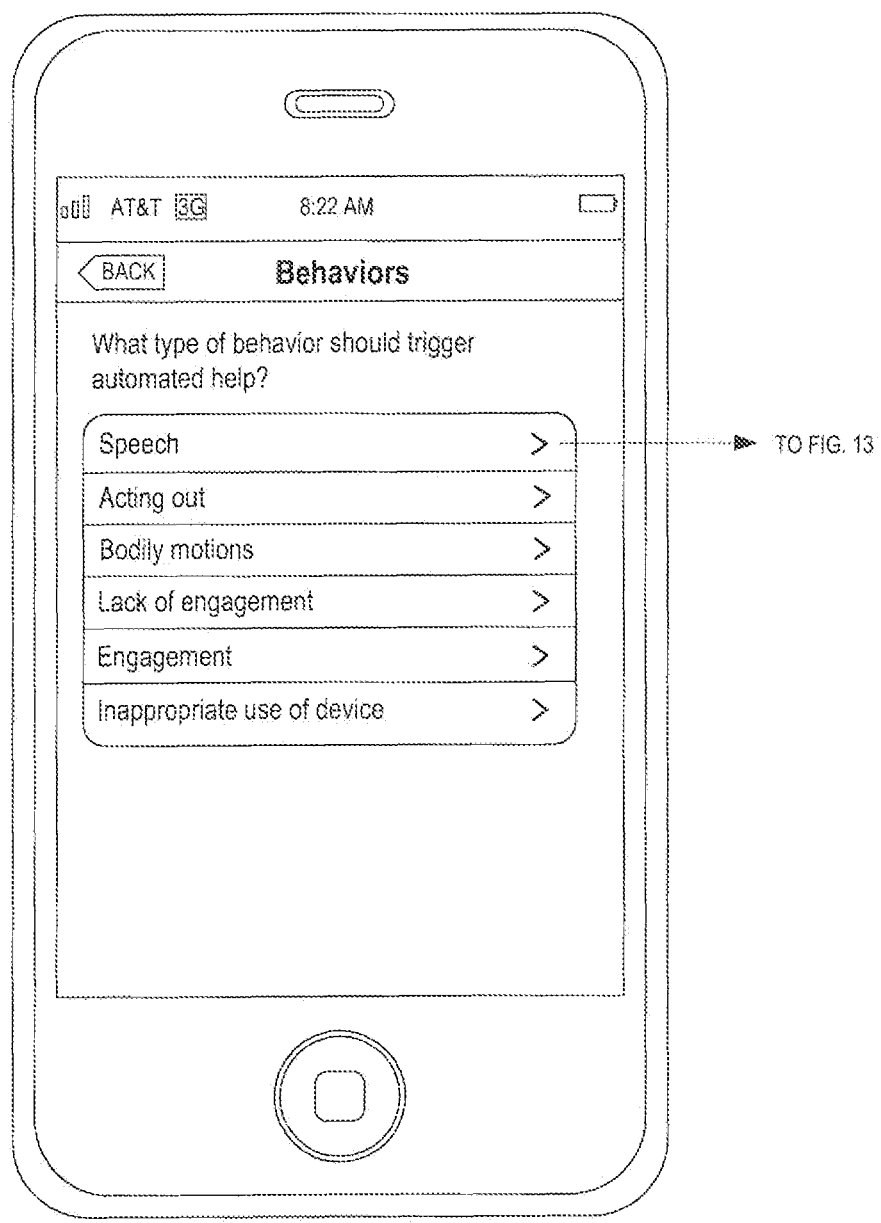
FIG. 12 illustrates a seventh screen shot associated with the flow chart of FIG. 5.

To aid the user in arriving at a specific criterion, subcategories or lists of options may be provided within each of the behavioral, environmental, and biological categories from which the user may choose (block 190, see also FIG. 12). Behavioral subcategories may include (but are not limited to): speech (i.e., uttering certain words, phrases or sounds), acting out (e.g., tantruming, screaming, shouting or crying; hitting or abusing a person or animal), bodily motions (e.g., rocking in place, covering ears or eyes, or falling to the ground), lack of engagement (e.g., "zoning out" or losing attention, staring at an object), engagement (e.g., proper use of or attention paid to the mobile terminal 10 or to another person), and inappropriate use or abuse of the mobile terminal 10 (e.g., slamming, pounding, dropping, or otherwise misusing the device).

Criteria related to the user's environment (not shown) may include (but are not limited to): the occurrence of noises and sounds, changes in lighting, temperature changes, changes in altitude, changes in geographic location, the detected presence of an object, and the detected presence of another person or being.

Criteria related to the user's body, biology or physiology (not shown) may include (but are not limited to): heart rate, blood pressure, blood glucose level, temperature, galvanic or electrodermal skin response, and pupil dilation. A more detailed description of the use of sensors, peripherals, peripheral devices, or other technologies associated with the mobile terminal 10 to determine whether such criteria have been satisfied is saved for the discussion of block 106 (of the flowchart of FIG. 5), which appears below.

Continuing the example, it is assumed that the user selects the option labeled "The user's behavior" as shown in FIG. 11. Accordingly, the discussion proceeds to FIG. 12 or a screen with similar functionality, which depicts the behavior-related subcategories described above.

Figure 13:
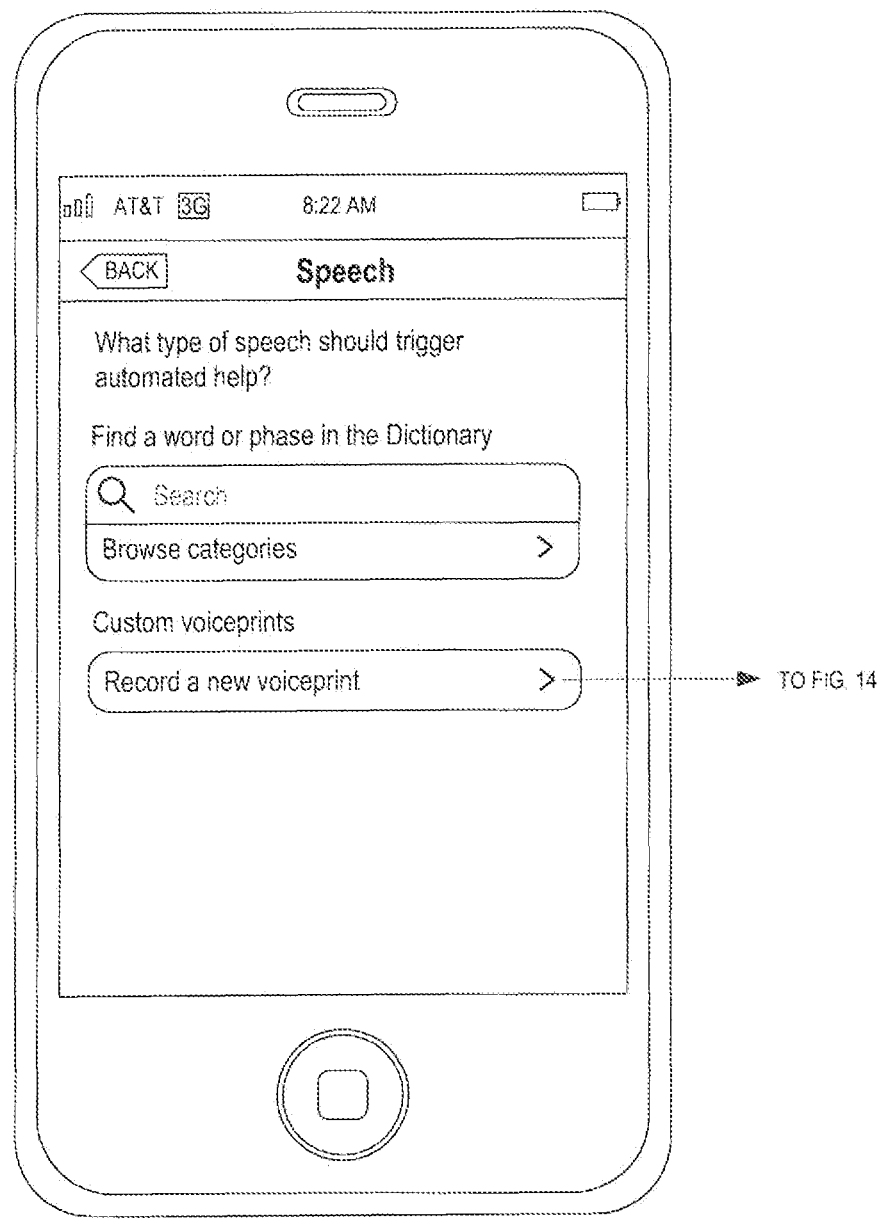
FIG. 13 illustrates an eighth screen shot associated with the flow chart of FIG. 5.

Assuming the user selects the "Speech" option, a screen such as that illustrated by FIG. 13 may be presented or a screen with similar functionality. Using a screen such as this, the caregiver may begin to configure a speech-related behavioral criterion (e.g., a word, phrase or other utterance that, when spoken by a user, will trigger automated communications) (block 192). Using one option, a caregiver may search or browse an already-existing "Dictionary" to select a particular word or phrase to be used as a trigger. Using another option, the caregiver may choose to record and save a custom voiceprint. Further, the caregiver may select a volume threshold such that when sounds (e.g., speech) is detected above or below the threshold, notifications to a remote caregiver and/or automated communications with the remote caregiver may be triggered (e.g., if a disabled person who is carrying mobile terminal 10 screams more than once within a given minute, then automated communications with a remote caregiver may be triggered).

Figure 14:
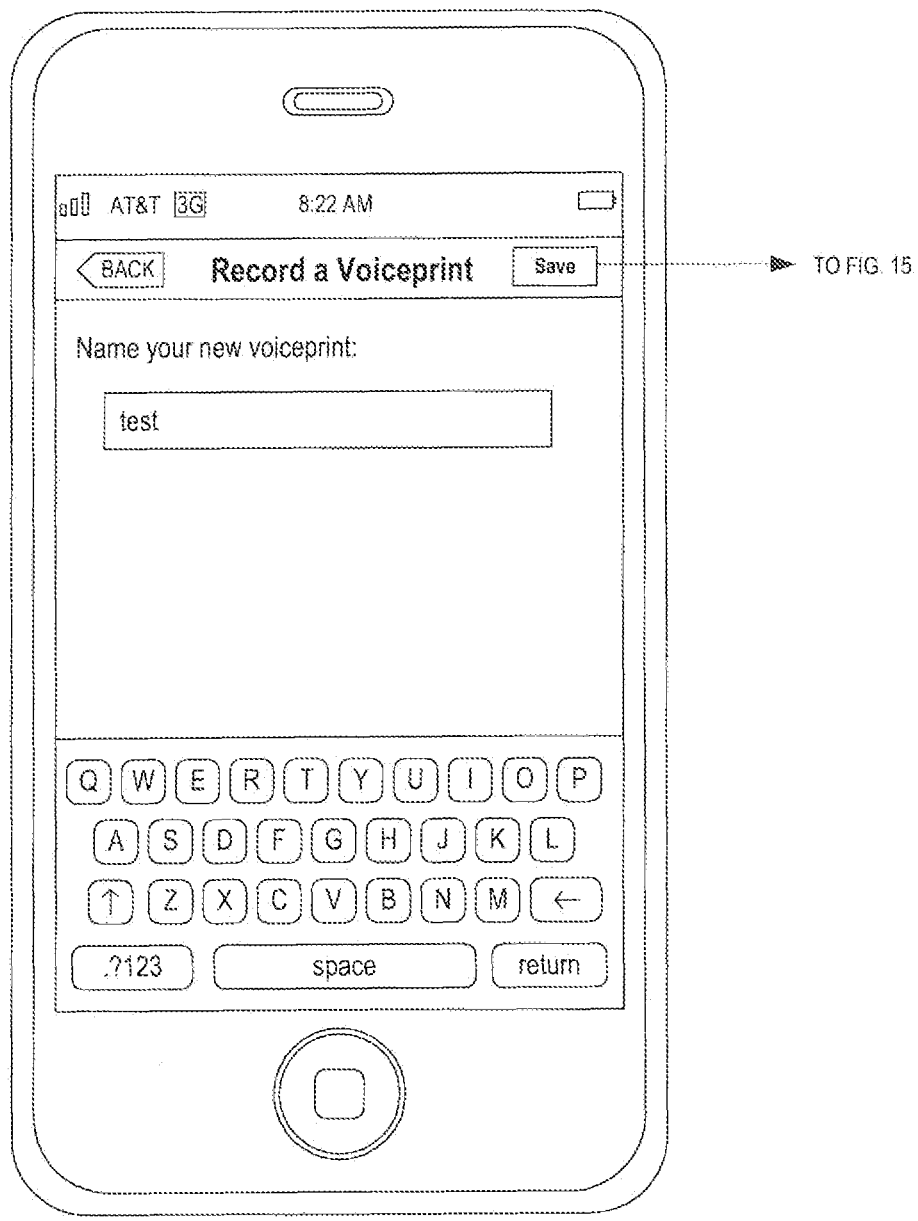
FIG. 14 illustrates a ninth screen shot associated with the flow chart of FIG. 5.

If the caregiver selects the latter option, a screen such as that of FIG. 14 or one having comparable functionality may be shown, enabling the user to enter a name for the new voiceprint through the user interface (e.g., a touch keypad or hardwired keys). After the user selects the "Save" option shown by FIG. 14, a screen such as that of FIG. 15 (or one having comparable functionality) may be output.

Figure 15:
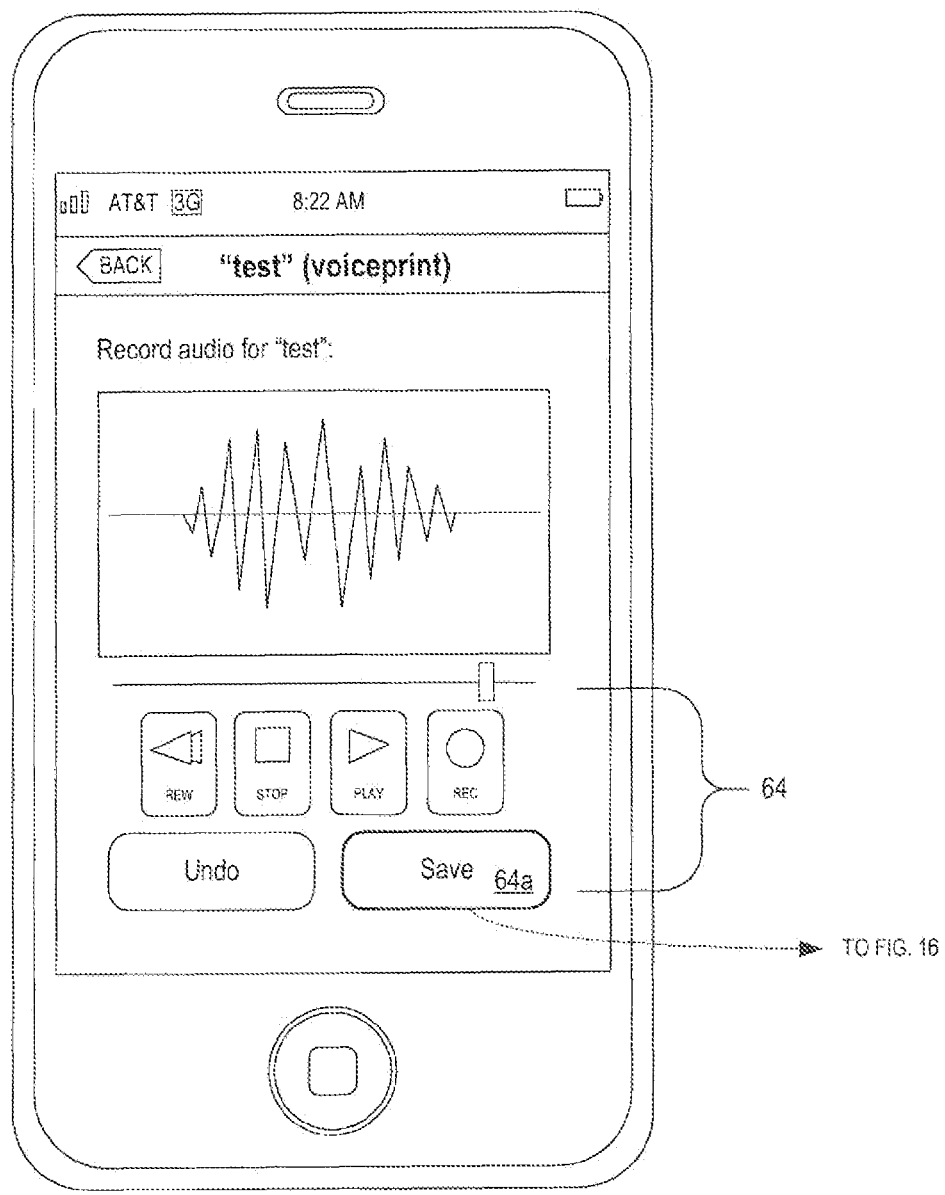
FIG. 15 illustrates a tenth screen shot associated with the flow chart of FIG. 5.

The screen of FIG. 15 allows a user to record and save a customized voiceprint (in this example, for the word "test"). Controls 64 allow the user to Rewind, Stop, Play, Record, Skip (to a particular point within a recording), Undo and Save. Audio may be recorded by an integrated microphone 26 of the mobile terminal 10, by a lapel microphone 58e, or by another microphone in communication with the mobile terminal 10 or computer 54. Once a voiceprint is saved (control 64a), the voiceprint may be added to the software's internal dictionary (such that the voiceprint can be later discovered using the search and browse mechanisms shown in FIG. 13). The voiceprint may be recorded by the caregiver or by the disabled individual (the latter may be preferred if it is indeed the disabled individual's utterance of the word or phrase that should be used to trigger automated communications). Voice recognition functionality as it pertains to computer 54 and mobile terminal 10 is well known in the art, with sophistication and accuracy improving over time. For example, using tools readily available in the APPLE® IPHONE™ software development kit, NUANCE COMMUNICATIONS, INC have developed a software application for the IPHONE called DRAGON DICTATION. The application allows users of the IPHONE™ to dictate common speech; the speech is then recognized so as to produce (i) text (e.g., saved to a notepad) or (ii) a command to execute a particular software function.

Continuing with the example and assuming the user has selected the "Save" control 64a, the user has now specified a trigger condition (i.e., an utterance of the word "test") that should be used to establish automated communications. However, at this point in the process of creating an automated help rule, the user has yet specify (i) a coverage period that should pertain to the rule (e.g., the software should "listen" for the word "test" between the hours of 7 a.m. and 5 p.m. on Mondays), (ii) one or more specific remote caregivers that should be contacted (e.g., contact "Mom" at a particular phone number if the word "test" is detected), and (iii) any media that should be utilized as part of the automated communication (e.g., pictures, text, audio or video that should be incorporated within an email, text message, or phone call). Within the context of the ongoing example, each of these steps will be described in turn.

Figure 16:
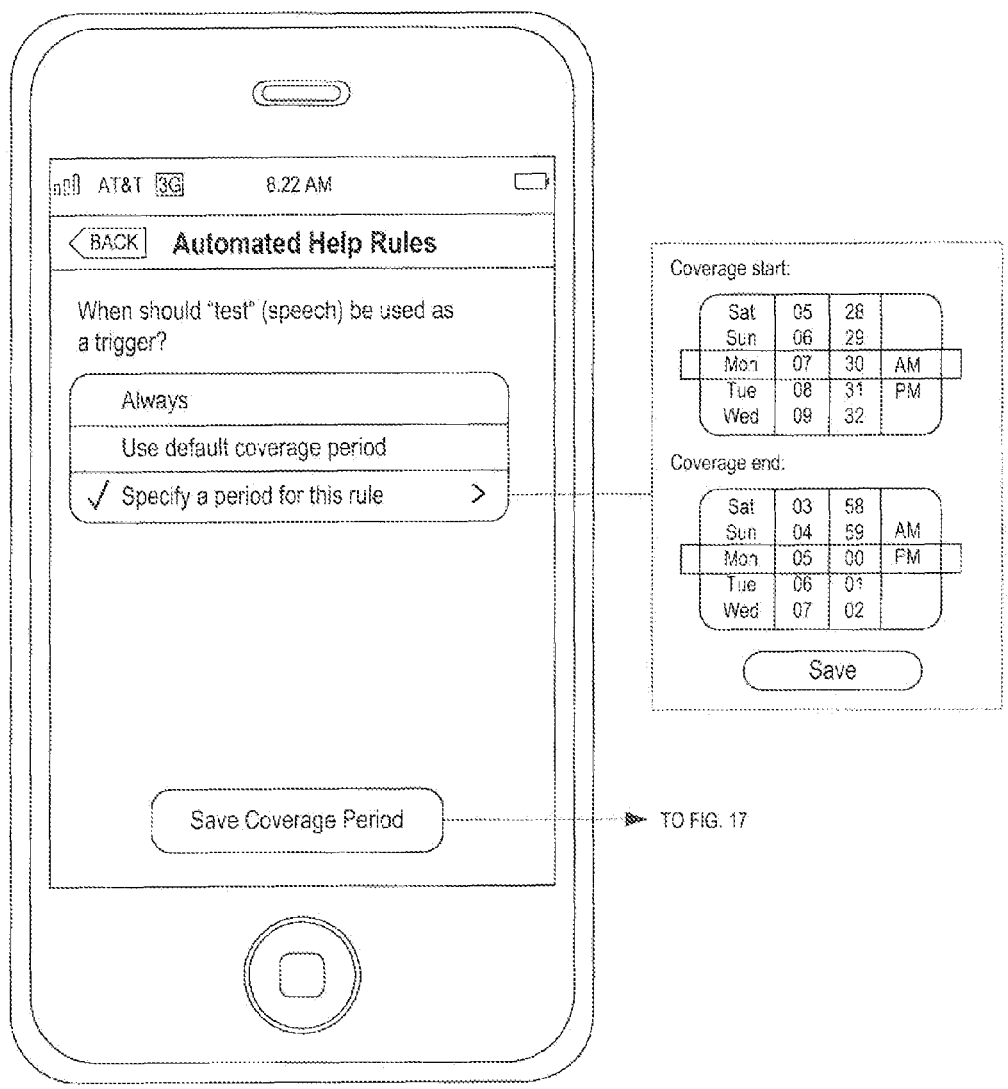
FIG. 16 illustrates an eleventh screen shot associated with the flow chart of FIG. 5.

The screen of FIG. 16 (or one having comparable functionality) presents options for configuring a coverage period in association with the automated help rule (block 194). The user may specify that the rule should be in effect as follows: (i) "Always", (ii) "Use default coverage period" (i.e., as specified using the "Create/Edit a Profile" screen of FIG. 8), or (iii) "Specify a period for this rule" (i.e., allowing the user to input a coverage start and a coverage end using an interface similar to that shown). In the example, the user specifies an applicable period, and then selects the "Save Coverage Period" option, advancing the ongoing example to FIG. 17.

Figure 17:
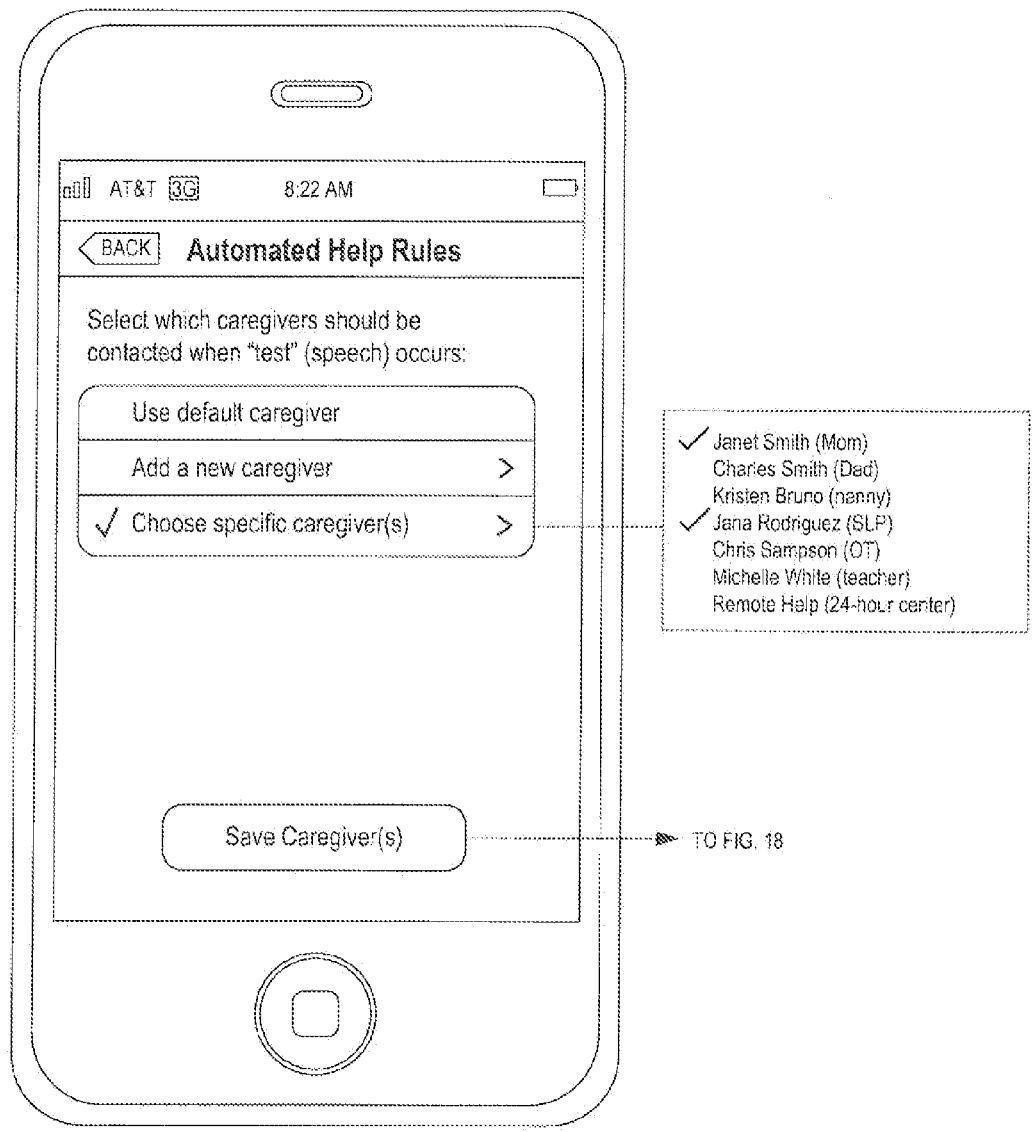
FIG. 17 illustrates a twelfth screen shot associated with the flow chart of FIG. 5.

Using a screen such as that of FIG. 17 (or one having comparable functionality), the user specifies one or more caregivers to be contacted (block 196) in association with the automated help rule. The user may select options such as: (i) "Use a default caregiver" (i.e., as specified using the "Create/Edit a Profile" screen of FIG. 8), (ii) "Add a new caregiver" (i.e., entering data as shown by FIG. 8), or (iii) "Choose specific caregiver(s)" (i.e., from a list as shown). Thus, the user may instruct that one or more particular caregivers should be contacted if the specified trigger condition (e.g., an utterance of the word "test" during the applicable coverage period) is satisfied.

Figure 18:
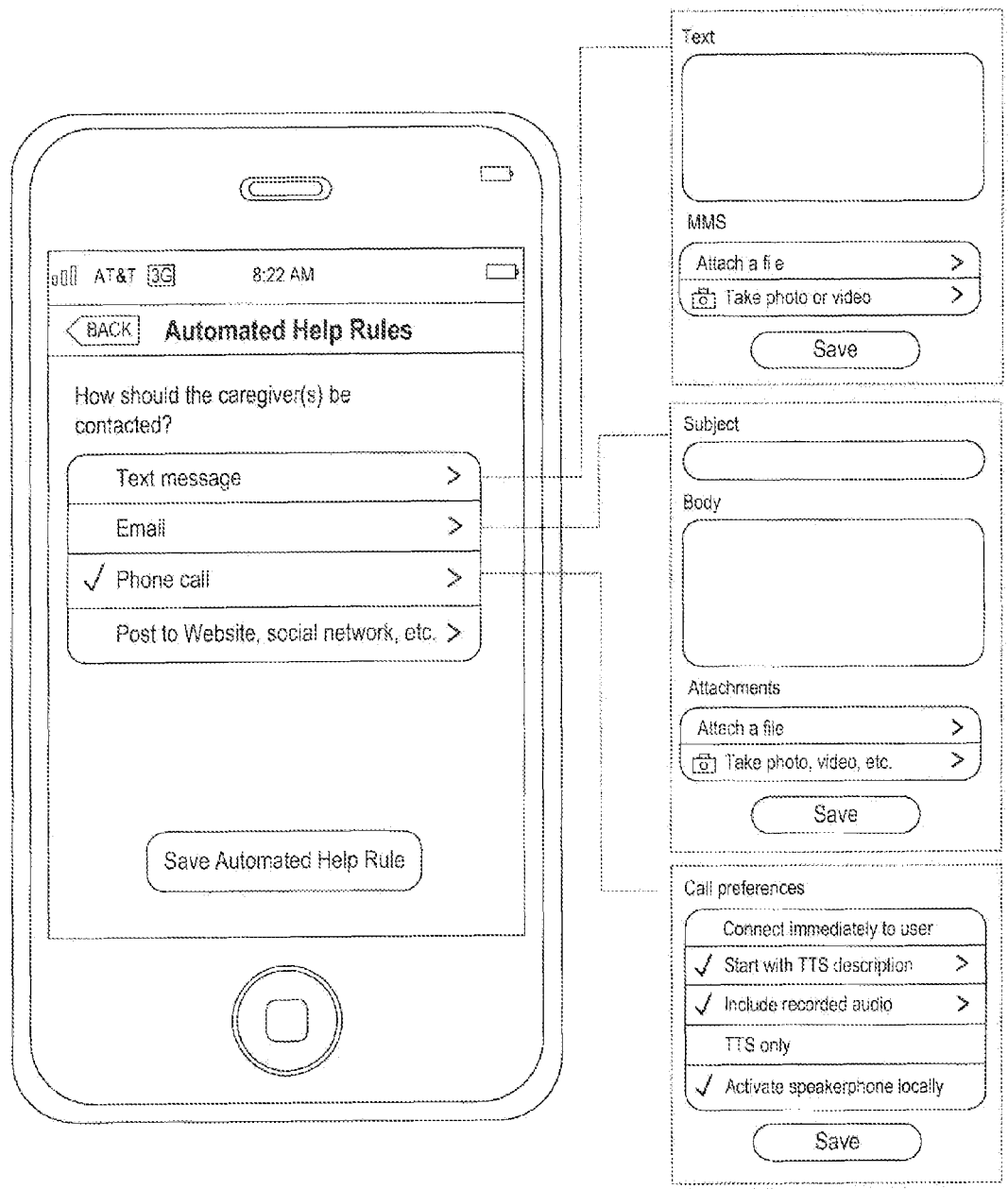
FIG. 18 illustrates a thirteenth screen shot associated with the flow chart of FIG. 5.

Continuing the example and assuming the user selects the "Save Caregiver(s)" option, a screen such as that of FIG. 18 (or one having comparable functionality) may be presented. The screen allows the user to identify one or more communication types which should be utilized when contacting a caregiver (block 198), including text messaging, email, a phone call, and post to a Website (e.g., a blog, a discussion forum designed as a support group for those affected by a particular disability, a site maintained by a 24-hour "Remote Help" service that operates in conjunction with the software of the present disclosure), social network (e.g., Twitter, Facebook, a network designed as a support group for those affected by a particular disability such as iAbida.com or FoggyRock.com), or the like.

The user may then specify the content of the communication to the remote caregiver (block 200). When configuring the content of an automated text message (or instant message), the user has the option to write and save text (e.g., a textual description of the situation that has resulted in the automated text message being sent), to attach a picture or video file already stored within the memory of the mobile terminal 10, or to create and attach a new picture or video. When configuring an automated email message, the user has the option to write a subject and a body, to attach a media file already stored within the memory of the mobile terminal 10 (e.g., the user's utterance of the word "test," which served as a trigger for automated communications in this particular example, is recorded and attached as an electronic sound file to the email), or to create and attach a new media file. When configuring phone call preferences, the user may select options such as "Connect immediately to the user" (i.e., meaning that once the call is placed to the caregiver, if the caregiver answers, a telephone call between the mobile terminal and the caregiver should begin immediately), "Start with TTS description" (e.g., allowing the user to type a text message which, using Text-to-Speech (TTS) technology, will be read aloud by a synthesize voiced at the start of the call), "Include recorded audio" (e.g., at the start of the call, an audio recording of the disabled individual's utterance of the word "test" is output, such that the caregiver can hear the context within which the word was spoken), "Call only" (e.g., a call is placed that, when answered by the caregiver, results only in a synthesized TTS voice describing the purpose and context of the call, without connecting (or before connecting) the mobile terminal 10 directly to the caregiver for a live telephone call), "Activate speakerphone locally" (e.g., the mobile terminal 10 placing the call should automatically enable its speakerphone capability when placing the call), and "Listen only" (not shown; a one-way connection allowing the caregiver only to hear audio from a disabled person's mobile terminal). While not expressly shown by FIG. 18, certain fields may be pre-populated with text (e.g., based on already-provided data related to a profile and an automated rule, the body of an email is pre-populated with "Remote help has detected that Jimmy Smith has said the word 'test'"; the user can simply save this description, or edit and subsequently save it). After configuring such communications preferences, the user selects the "Save Automated Help Rule" option (block 202) such that the new rule is created and added to the list of saved rules shown by FIG. 9. The user may then back out of the program either by exiting or hitting the "back" command until the user reaches block 102 where the user may load a profile and begin monitoring as described in greater detail below.

It should be appreciated that if the user instead selects "Edit an Existing Profile" (block 154), the user may see a screen similar to that shown in FIG. 8, but with fields already populated with previously stored information that the user may edit by selecting an appropriate field and changing the information as desired. Once the user is done making changes, the user may save the edited profile either overwriting the existing profile or using a command such as "save as" so that the new rule is in addition to the previously existing rule. Once the new profile is saved, the user may exit the program or return to block 102 as previously described.

With the rule now programmed, the process depicted by the flowchart of FIG. 5 continues to decision block 106, wherein it is determined whether the criteria saved in association with the rule have been satisfied. If the criteria are satisfied—i.e., the required behavior, environmental change, or body state has been detected via a sensor associated with the mobile terminal 10, and the current time and date falls within the specified coverage period—the process continues to block 108, wherein communications are initiated between the mobile terminal 10 and the remote caregiver. In one embodiment, if the criteria are not satisfied, the process loops at decision block 106 (notwithstanding specified coverage periods or other instructions saved in association with an automated help rule, the software continually determines whether criteria are satisfied).

A variety of sensors, peripherals, peripheral devices, and other technologies associated with the mobile terminal 10 may be employed when determining whether a specified behavior, environmental change, or body state has been detected. Some examples will now be set forth in which particular technologies are paired with the detection particular behaviors, environmental changes, and body states. Though an example is not provided for every possible pairing, this should not be construed as limiting the capacity of the software to employ all available technologies in detecting whether criteria have been satisfied.

In one example of detecting speech, an integrated microphone 26 is used to detect that a particular word or phrase has been spoken. In another example, a peripheral lapel microphone 56e is used to detect the word or phrase. In any case, an uttered word or phrase may be "matched" to a voiceprint stored within electronic memory. The voiceprint may be generic (e.g., the speech criterion is satisfied the word or phrase may be spoken by any person), or associated with a particular person (e.g., the speech criterion is satisfied only if the word or phrase is spoken by a particular person). Various technologies for so-called biometric voiceprint matching using mobile terminals are known in the art (e.g., the PHONEFACTOR system manufactured by PHONEFACTOR, INC of Overland Park, Kans. utilizes such technology).

In some embodiments, a criterion may be satisfied if a threshold amount of unintelligible or incoherent speech is detected. For example, if words detected through mobile terminal 10 (e.g., from a particular user, detected through voice print technology) fail a grammatical test (e.g., similar to a grammar check in a word processing program), they may be deemed "incoherent" such a criterion may be satisfied.

In one example of detecting that a user of the mobile terminal 10 is acting out or otherwise upset, an integrated microphone 26 is used to detect screaming, shouting or crying. In another example, a peripheral lapel microphone 56e may be used to detect such noises. In some embodiments, for a criterion to be satisfied, noise must be above a threshold decibel level (e.g., as specified by a caregiver). In some embodiments, a caregiver may record such sounds as produced by a disabled individual in a manner similar to that described previously with respect to recording speech; the recording may then be used similar to a "voiceprint" for establishing a benchmark against which such sounds may be compared during the detecting process. In other examples of detecting maladaptive behavior or tantruming, physical acts may be considered. For example, in some embodiments, certain types of bodily motion may be indicative of acting out (e.g., a user wearing a ring 58d, watch 58c or other peripheral device attached to an arm may engage in aggressive arm motions for a period of time, the motions detected by a sensor embedded within the peripheral device). Also, physical interaction with the mobile terminal 10 may be considered. For example, a pressure sensor associated with a button or screen of the mobile terminal 10 may detect an excessive amount of force, an accelerometer 34 may detect excessive motion, a light sensor may detect that a pattern indicative of abusive behavior (e.g., the light sensor is repeatedly covered and uncovered), and/or a vibration sensor may detect an impact. In some embodiments, combinations of several of the above behaviors may lead the software to conclude that criteria have been satisfied (e.g., simultaneous crying above a threshold decibel level and physical mishandling of the mobile terminal 10 are illustrative of tantruming behavior).

In some embodiments, the disabled user of mobile terminal 10 may be randomly or periodically prompted by mobile terminal 10 to perform a task, such as answering a multiple choice question (e.g., "when is your birthday?"). If the task is not performed or is performed incorrectly, criteria may be satisfied (e.g., such that automated communications with a remote caregiver ensue). Such an embodiment may be particularly beneficial where disabled users of mobile terminals suffer from afflictions which present episodically, such as Alzheimer's syndrome, as such users may be tested to determine their then-current state of functioning. That is, if the disabled user fails to perform the task appropriately, it may be inferred that caregiver assistance may be appropriate. The remote communication triggering embodiments of the present disclosure may then facilitate such remote caregiver assistance through mobile terminal 10.

In some embodiments, the detection of certain types of bodily motions may cause criteria to be satisfied. Various types of bodily motions may be detected using sensors described herein. In one example, bodily motions of rocking in place or shaking of the head are detected using eyeglasses 58a (e.g., a motion sensor, infrared sensor, RFID transponder, or other sensor is embedded within the eyeglasses, communicating relative head position to the mobile terminal 10). Waving of the hand, flailing of the arms, punching, hitting, kicking or running may be detected by peripheral devices attached to arms or legs. Covering of the ears or eyes may be detected using a combination of sensors (e.g., eyeglasses 58a and ring 58d). Further, in some embodiments, any of the above motions may be detected without the use of a peripheral device. For example, an integrated camera 24 or motion sensor oriented toward the arms (e.g., as facilitated by the hanging of mobile terminal 10 around a user's neck using lanyard 62) may detect excessive arm motions. Accelerometer 34 and/or a vibration sensor may detect the mobile terminal 10 (and perhaps thus its user) has fallen to the ground.

In some embodiments, a criterion may be satisfied if it is determined that a user is sufficiently engaged with the mobile terminal 10, a current activity, or another person. In one example, eyeglasses 58e are used to determine that the user's gaze is oriented toward the mobile terminal 10 (e.g., using camera 60, an RFID transponder, an infrared sensor, or the like). In another example, a separate peripheral device associated with an object or person (e.g., an RFID receiver or other sensor carried or worn by a physically present caregiver, such as a teacher) may be used in conjunction with eyeglasses 58e (e.g., worn by a disabled individual) to determine that a disabled individual's gaze is indeed oriented in the direction of the object or person (e.g., for at least a threshold percentage of time over the course of a particular time period). In some embodiments, it may be desirable to determine whether a user of the mobile terminal 10 is engaged in social activity (or at least within the company of other persons). In one example, a user of the mobile terminal 10 may be considered sufficiently socially engaged if a microphone 26 (or another microphone such as lapel microphone 58e) detects at least a minimum level of speech activity or ambient volume level during a specified period of time. In another example, one or more sensors or other technologies associated with a first mobile terminal 10 (e.g., carried by a disabled individual) may be used to determine that a second mobile terminal 10 or peripheral device (e.g., carried by another individual) is present. Many technologies may be employed to accomplish such a goal, including a motion sensor, infrared sensor, RFID, GPS, triangulation of geolocation using WiFi or cellular network nodes. In one such embodiment, a first and second mobile terminal 10 may be registered (e.g., using software of the present disclosure) as "buddy" or "friend" devices (e.g., to facilitate the determination that a specific caregiver "friend" is nearby a disabled individual at a particular time). In another embodiment, using GPS, WiFi triangulation, and/or cellular triangulation, the current location of a mobile terminal 10 is determined to be in an area known to be social or well-populated in nature (e.g., a school, a coffee shop, a library).

Conversely, a criterion may be satisfied if it is determined that a user is not sufficiently engaged with the mobile terminal 10, a current activity, or another person. In such embodiments, criteria described in the immediately preceding paragraph may be reversed. For example, eyeglasses 58e are used to determine that the user's gaze is oriented away from the mobile terminal for a particular duration of time. In another example, a separate device (e.g., a "buddy" or "friend" mobile terminal 10) is not detected within a specified range.

In some embodiments, the detection of a specific environmental noise or sound may satisfy a criterion. Such noises and sounds may be detected in a manner similar to that described above with respect to speech. Various systems are known for classifying environmental sounds. One such system, the SOLAR (Sound Object Localization and Retrieval) system as developed by researchers at the UNIVERSITY OF ILLINOIS AT CHAMPAGNE-URBANA, compares sounds detected by microphones to a vast database of sound types, so as to distinguish car horns, dog barks, trains, human voices, etc. Software of the present disclosure may communicate with such a database using an API.

In some embodiments, the detection of a specific amount of light in the environment proximate to the mobile terminal 10 may satisfy a criterion. For example, a light sensor may detect a particular abundance or lack of light during a period of time (e.g., indicating that the mobile terminal 10 is in direct sunlight or in a dark environment).

In some embodiments, the detection of a specific environmental temperature may satisfy a criterion. For example, a thermometer may be used to determine that the mobile terminal 10 is in a particularly cold environment (e.g., beneath 40° F.). In another example, a directional temperature sensor may determine that a nearby object is at or above a threshold temperature (e.g., a nearby stove, fire, or other object is excessively hot).

In one embodiment, the detection of an altitude change may satisfy a criterion. For example, an altimeter may be used to determine that an altitude associated with the mobile terminal 10 has dropped rapidly within a short period of time.

In some embodiments, data concerning the geographic location of the mobile terminal 10 may satisfy a criterion. As is known in the mobile terminal art, a current geographic location may be determined using GPS technology, triangulation using WiFi or cellular network nodes, or the like. In one example, a criterion may be satisfied if the mobile terminal 10 is within proximity of a particular geographic location at a particular time. In another example, a criterion may be satisfied if the mobile terminal 10 has strayed outside of a geographic "safe zone" expressly programmed by a caregiver (e.g., a 10 mile radius surrounding school and home). In another example, a criterion is satisfied if the mobile terminal 10 has been detected within sufficient range of three separate geographic areas within a particular time (e.g., a child carrying the mobile terminal has gone from school, to an after school program, and finally to home on a particular afternoon). In another example, a criterion is satisfied if the mobile terminal 10 has been taken to a "new" geographic location as per a database storing previously visited locations.

In some embodiments, the detection of a nearby person or object may satisfy a criterion. In one example, as described, such a person or object may wear or carry a device equipped with a sensor, and the person may in turn communicate the presence of the object or person to the mobile terminal 10. In another embodiment, a microphone 26, 58e may be used to detect a voiceprint associated with another person (e.g., a specific caregiver). In another embodiment, an integrated camera 24 (or camera associated with a peripheral device, such as camera 60) may detect the presence of a particular person or object. For example, an image comparison search engine may be employed, allowing for images captured by a camera to be matched with those included within a large online database. An example of such technology is the TIN-EYE REVERSE IMAGE SEARCH ENGINE created by IDEE, INC of Toronto, Canada, which includes a commercial API allowing third party software applications (such as the software of the present disclosure) to communicate with the database.

In some embodiments, a criterion is satisfied based on heart rate data associated with a user of the mobile terminal 10. For example, a user's heart rate may be monitored through the employ of a patch 58b, wristwatch 58c, ring 58d, or other wearable device that may detect and transmit such data (e.g., a bracelet, anklet, wristband, etc.). A criterion may be satisfied by a specified increase in, decrease in, or consistent level of beats per minute (e.g., a user's heart rate remains beneath 60 beats per minute for a period of time).

In some embodiments, a criterion is satisfied based on blood pressure data associated with a user of the mobile terminal 10. For example, a user's blood pressure may be monitored through the employ of a patch 58b, wristwatch 58c, ring 58d, or other wearable device, such as an armband. A criterion may be satisfied by a specified increase in, decrease in, or consistent level of pressure (e.g., a user's blood pressure spikes above 130/80). In one example, a caregiver sets a coverage period such that it aligns with a period shortly after a disabled individual is scheduled to take blood pressure medication; if blood pressure rises during the coverage period, it may be inferred that the individual has forgotten to take a dosage of medication.

In some embodiments, a criterion is satisfied based on blood glucose data associated with a user of the mobile terminal 10. For example, a user's blood glucose may be monitored using technologies described previously in this disclosure. A criterion may be satisfied by a specified increase in, decrease in, or consistent level of blood glucose (e.g., a user's blood sugar level drops beneath 60 mg/dL).

In some embodiments, a criterion is satisfied based on body temperature data associated with a user of the mobile terminal 10. For example, a user's body temperature may be monitored using a peripheral device described herein (e.g., a patch 58b, wristwatch 58c, or ring 58d comprising an infrared or heat sensor). A criterion may be satisfied by a specified increase in, decrease in, or consistent body or skin temperature.

In some embodiments, a criterion is satisfied based on electrodermal or galvanic skin response (GSR) data associated with a user of the mobile terminal 10. Such data are used in the art to monitor and infer human emotions (e.g., fear, anger, anxiety, startle response, orienting response). GSR data may be read and transmit using a peripheral device, with the device enabled to measure electrical resistance between two points on the user's skin. Commercially available sensors such as the GSR 2™ as produced by THOUGHT TECHNOLOGY LTD of Plattsburgh, N.Y. may be adapted for purposes of this disclosure. A criterion may be satisfied based on an increase or decrease in electrodermal activity (e.g., a sharp increase may suggest a user has grown fearful or anxious).

Having described a wide array of criteria that may trigger automated communications, and manners for detecting the satisfaction of such criteria, the discussion now turns to block 108 of the flowchart of FIG. 5, wherein automated communications to a remote caregiver are initiated. As described previously with respect to FIG. 18, a user programming an automated help rule selects one or more communication methods (including text messaging, email, a phone call, and posts to a Website, social network, or the like), and further configures preferences related to the communication (e.g., any multimedia content to be included as part of the communication). Thus, the communication as configured by the user in block 104 of FIG. 5 is now initiated in block 108.

Generally speaking, certain communication modalities may make particular sense when matched to certain criteria for triggering automated communications (e.g., more urgent circumstances may require a phone call or text message, whereas less urgent circumstances may be handled by email or by posting to a social network). Rather than walk through each possible arrangement, three particular examples will now be described wherein a caregiver programs criteria for an automated help rule, the criteria are satisfied, and automated communications are initiated as instructed.

Figure 19C:
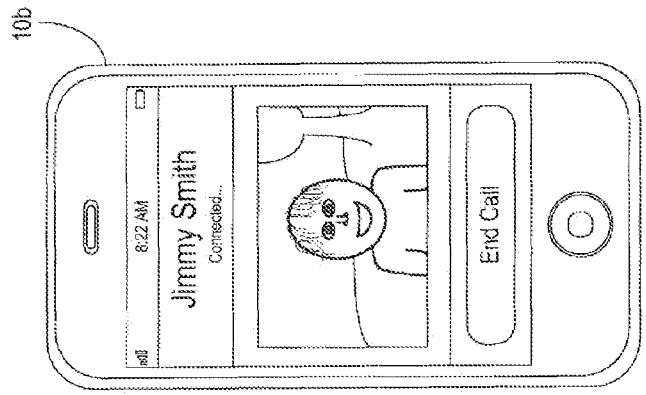
FIGS. 19A-C illustrate a fourteenth, fifteenth and sixteenth screen shot associated with the flow chart of FIG. 5, as well as a peripheral device which may interface with a mobile terminal.
Figure 19B:
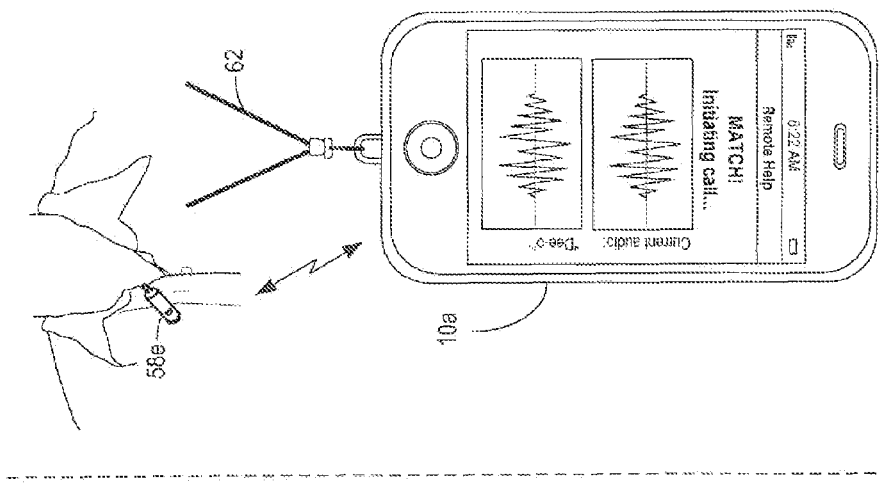
Figure 19A:
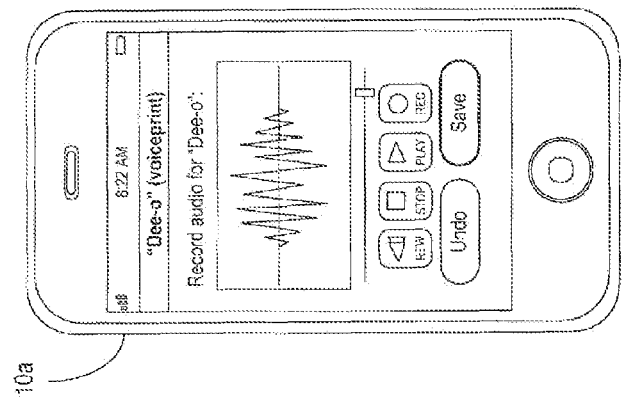

A first example is illustrated by FIGS. 19A-C. In this example, a caregiver has programmed an automated help rule based on speech as uttered by a user of the mobile terminal 10 (a behavioral consideration). Using software of the present disclosure, the caregiver first configures a mobile terminal 10a, which will be carried and used primarily by a disabled individual. As shown by FIG. 19A, the caregiver records a word or phrase to be used as a trigger in establishing automated communications. In this example, the caregiver has recorded and saved a disabled child's utterance of the phrase "Dee-o"; the phrase that may sound meaningless to those who do not know the child, but the caregiver understands this phrase to mean "all done" (the child would like the current activity, such as eating, to end). Though not shown by FIGS. 19A-C, the caregiver then utilizes the software to program any applicable coverage periods, caregivers, or communication preferences associated with the automated help rule. In this case, the caregiver has indicated that the form of communication should be a phone call, placed to a phone number corresponding to mobile terminal 10b, which will be carried and used by the caregiver. Moving to FIG. 19B, the child (e.g., named Jimmy Smith) subsequently carries the mobile terminal 10a (optionally using lanyard 62 to hang the device around his neck), and indeed utters the phrase "Dee-o" while being fed a fruit snack at an after-school program, indicating a desire to stop eating the snack. Upon detecting the utterance of the phrase (through the optional use of lapel microphone 58e), the software determines that the programmed criteria of an automated help rule have been satisfied (e.g., not only has the phrase been spoken, but it has been spoken at least five times within several minutes during a specified coverage period), and accordingly initiates automated communications by calling mobile terminal 10b. Depending on the call preferences previously selected by the caregiver, the caregiver may immediately be connected to mobile terminal 10a for a live phone call; in this example, it is assumed that the caregiver has selected both the "Start with TTS description" and "Include recorded audio" call options (as shown by FIG. 18). Thus, upon answering the call, the caregiver first hears a computerized voice read aloud "This call has been placed because Jimmy Smith has spoken a word you have selected as a Remote Help trigger. Please listen as a recording of Jimmy will now be played". Continuing to listen, the caregiver then hears a recording (captured by mobile terminal 10a and transmit to mobile terminal 10b over the call) of the disabled child repeatedly uttering the phrase "Dee-o" and then saying "Fruit snack". Because the caregiver previously selected an "Activate speakerphone locally" option, the caregiver may then speak into mobile terminal 10b such that all individuals proximate to mobile terminal 10a may hear. At this time, the caregiver may translate for the disabled child, informing those physically present that the child would like to stop eating fruit snacks. Though mobile terminals 10a and 10b appear similar, it should be understood that in practice different mobile terminals may be used.

Figure 20C:
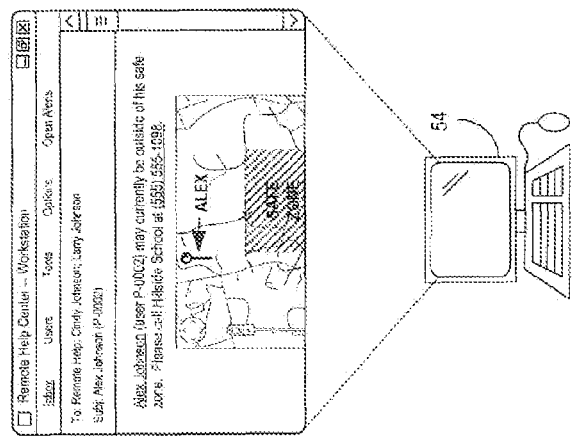
FIGS. 20A-C illustrate a seventeenth and eighteenth screen shot associated with the flow chart of FIG. 5, as well as an example map depicting a geographic location of a mobile terminal.
Figure 20B:
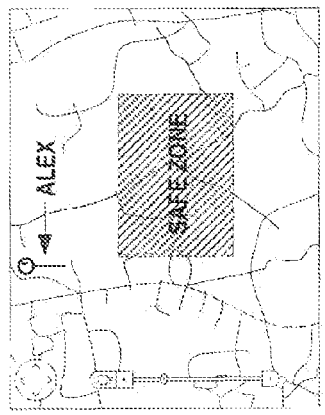
Figure 20A:
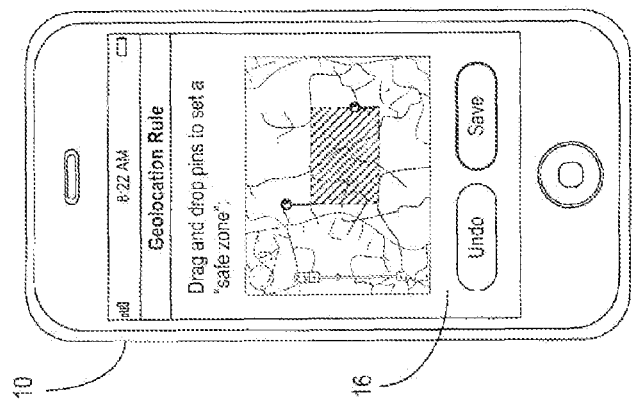

A second example is illustrated by FIGS. 20A-C. In this example, a caregiver has programmed an automated help rule based on the geographic location of the mobile terminal 10 (an environmental consideration). The caregiver begins by configuring mobile terminal 10, which will be carried and used primarily by a disabled individual (e.g., Alex Johnson). To configure an automated help rule based on the geographic location of the mobile terminal 10, the caregiver may navigate a series of menus to arrive at the screen depicted by FIG. 20A. (Specific menu options are not shown, but they may appear similar to those of FIGS. 12 and 13, albeit with categories and options related to the user's environment/location rather than the user's behavior/speech.) Using the screen of FIG. 20A, the caregiver is encouraged to create a geographic "safe zone". This may be done utilizing touch screen display 16 as shown (e.g., the user drags and drops two pins across a map, and presses "Save," creating the zone) or another method (e.g., entering an address, and then setting a radius of a certain number of miles surrounding the address). Regardless, after the safe zone is configured and saved, the mobile terminal 10 is given to the disabled individual. Indeed, the disabled individual has taken the wrong bus home on a particular Wednesday afternoon, and as shown by FIG. 20B (a map indicating the safe zone and a pin signifying the current location of mobile terminal 10, as determined by GPS or another method described herein), this results in the mobile terminal 10 being taken outside of the safe zone during a specified coverage period. An automated help rule is triggered. Per the rule, a few different communications are triggered: (i) a phone call to the caregiver's spouse, who works from home on Wednesdays and is likely nearby (not shown), and (ii) an email alert to a 24-hour Remote Help service retained by the caregivers (e.g., for a monthly service fee, which may be based on the number of automated help rules created by the primary caregivers). The alert is shown by FIG. 20C, which depicts a computer 54 controlled by an employee of the service. The employee is instructed to call the child's school in hopes of tracking down Alex (e.g., the school may contact the bus driver whose route corresponds with Alex's current location, as advised by the employee of the service).

Figure 21C:
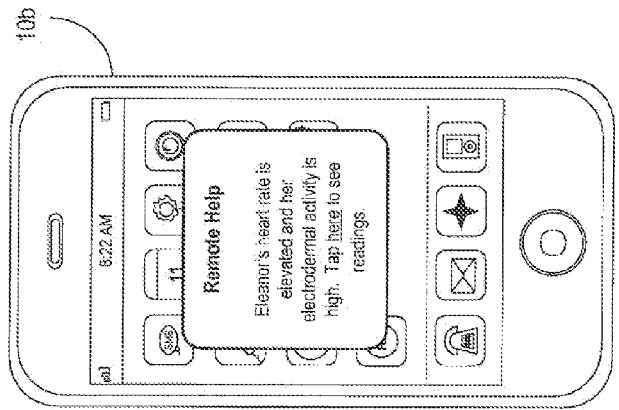
FIGS. 21A-C illustrate a nineteenth, twentieth and twenty-first screen shot associated with the flow chart of FIG. 5, as well as peripheral devices which may interface with a mobile terminal.
Figure 21B:
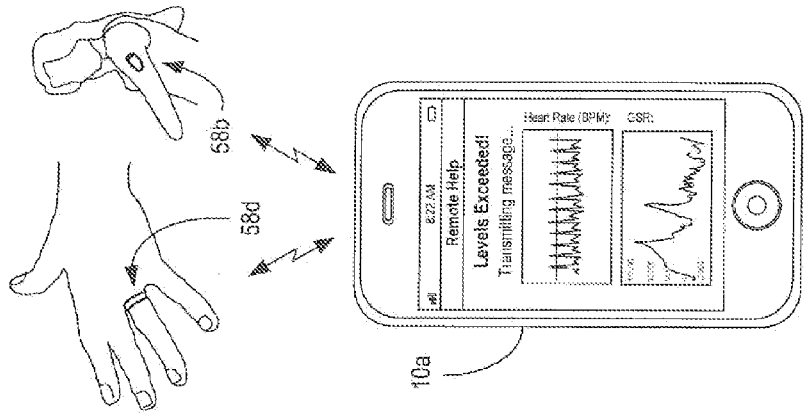
Figure 21A:
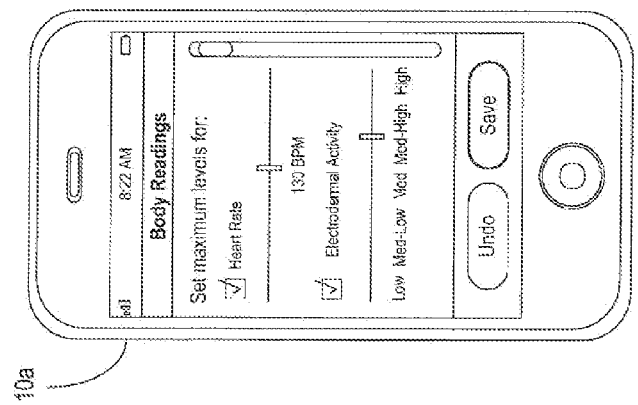

A third example is illustrated by FIGS. 21A-C. In this example, a caregiver (e.g., a psychologist or guidance counselor) has programmed an automated help rule based on heart rate and electrodermal activity data associated with a user of the mobile terminal 10a (considerations based on the user's body). The caregiver first programs threshold levels (e.g., 130 beats per minute for heart rate and "Med-High" for electrodermal activity) above which automated communications should be triggered. The caregiver also specifies a coverage period (e.g., a period when the mobile terminal user is expected to be relatively calm) and configures any other applicable options. The mobile terminal 10a is then given to a user, in this instance named Eleanor. Eleanor carries the mobile terminal, and equips a ring 58g to measure and transmit heart rate data and a patch 58b to measure and transmit electrodermal activity data. Eleanor, who suffers from chronic panic attacks and anxiety, feels nervous in advance of taking a high school exam. As her emotions intensify, her heart rate increases and her skin and muscle tissue begin to react. Based on input from the sensors, an automated communication is accordingly triggered (i.e., the thresholds are exceeded as illustrated by FIG. 21B). In this example, the caregiver's selected communication modality is that of text message to a mobile terminal 10b. As shown by FIG. 21C, the caregiver accordingly receives a text message on the screen of mobile terminal 10b (which again appears similar in look and feel to mobile terminal 10b, though different terminals may be used). The caregiver may respond by selecting a hyperlink to view the associated biometric data, and/or by sending a response text message to Eleanor's mobile terminal 10a (e.g., attempting to calm Eleanor down and assuring her not to be nervous about her exam).

As is demonstrated within the above examples, in some embodiments, a caregiver receiving a phone call, text message, or other form of automated communications may respond to the mobile terminal 10 that initiated contact. This optional step is shown as block 110 of the flowchart of FIG. 5. In one embodiment, receiving a response from a caregiver comprises answering a phone call placed by the mobile terminal 10. In another embodiment, receiving a response from a caregiver comprises placing a phone call (e.g., to an indicated number). A caregiver might also respond by sending a text message, sending an email, accepting a video conference invitation, or posting on a Web site or social network. At any rate, a caregiver may provide care instructions, therapy instructions, behavioral tips or suggestions, a translation of speech, history or background about the disabled individual, or any other pertinent data either directly to the disabled individual or to a physically present caregiver at this time.

Example audio responses from a remote caregiver include: (i) "Oh, Ms. Johnson, he's trying to say 'all done'! Maybe the texture of the finger paints are bothering him" such that the audio is output by a mobile terminal's speakerphone, (ii) "Edna, this is Chris from the Online Help Center. Please STOP what you are doing and take the medication in the BIG pill container. It says 'MORNING PILLS' on it," such that an elderly woman can be directly assisted in taking her medication, (iii) "Excuse me. My son has autism. He doesn't understand you. Please stop bullying him. I have a picture of you and will tell your mother about this next time I see her," such that the audio is output by a mobile terminal's speakerphone, (iv) "Whoever is listening, please get Allison away from the monkey bars! Her coordination is not good and I am very worried she will fall," such that the audio is output by a mobile terminal's speakerphone, and (v) "It's too bright! Wear your sunglasses!" such that an individual with sensory processing challenges is directly given guidance.

Example responses primarily involving text include: (i) "Chester, the mall is TOO LOUD and too busy for you. Please go take the bus back home" (sent via text message directly to Chester's mobile terminal), (ii) "Great job asking for help, Albert. Next time you can say 'My leg hurts' if that is what is bothering you" (as posted by a physical therapist in a response to an automated post from Albert on a social network), (iii) "Say 'THANK YOU' to the nice man" (sent via text message directly to an individual with Asperger's disorder who sometimes struggles in social situations), (iv) "Hi Ms. Johnson, it's Cassie's mom. I think she's struggling with her assignment right now because of the fluorescent lights. Can she do her assignment in the hallway?" (sent via instant messenger from a parent to a child's teacher), and (v) "Please find attached a sequence of pictures that should help guide Stephen through lunchtime" (sent from a therapist to a parent via email).

In some embodiments, responding to an automated communication may comprise forwarding or routing media associated with the communication to another person. In one example, a school nurse is notified via text message that a child has fallen outside during recess; on her way outside, she forwards the notification to a mobile terminal used by the child's parent. In another example, a staff member at a 24-hour remote help center reviews data about an elderly woman and determines the woman is somewhat far from home and may be lost; the staff member transmits an email message to the elderly woman's daughter informing the daughter of the woman's current location. In another example, parent is notified that his child is screaming, and sends text messages to all "friend" or "buddy" mobile terminals within a certain geographical proximity of the disabled individual's mobile terminal 10. For example, the parent may be permitted to send a text message to individuals near on the scene, reading "Please help Johnny if you are nearby. Unfortunately the more he screams, the more people look. Please encourage people not stare at him and he should be fine. Thanks for understanding." Or, by way of another example, the parent may send a text message to individuals reading "Dear Fairfield Special Needs Parent Support Group: Johnny Smith has left his safe zone, and I am stuck in traffic. He is at 234 Main Street right now. Can someone please pick him up? Please reply-to-all if so. Thanks, Fred Smith."

In one embodiment, different versions of software of the present disclosure may exist. In particular, it is contemplated that one version of the software may be designed to operate on a mobile terminal 10 used primarily by a disabled individual, whereas another version may be designed to operate on a mobile terminal 10 used primarily by a caregiver (e.g., "Remote Help" vs. "Remote Help for Caregivers"). The two versions might be thought of as companions to one another, and may be linked or co-registered so as to facilitate communications between the mobile terminals. For example, in one embodiment, a caregiver may purchase a copy of each version as a bundle or package (hardware may or may not be included). The caregiver may then configure each version of the software, saving relevant contact information and settings in each, and ultimately maintaining a caregiver-specific version on his or her own mobile terminal 10.

Figure 22:
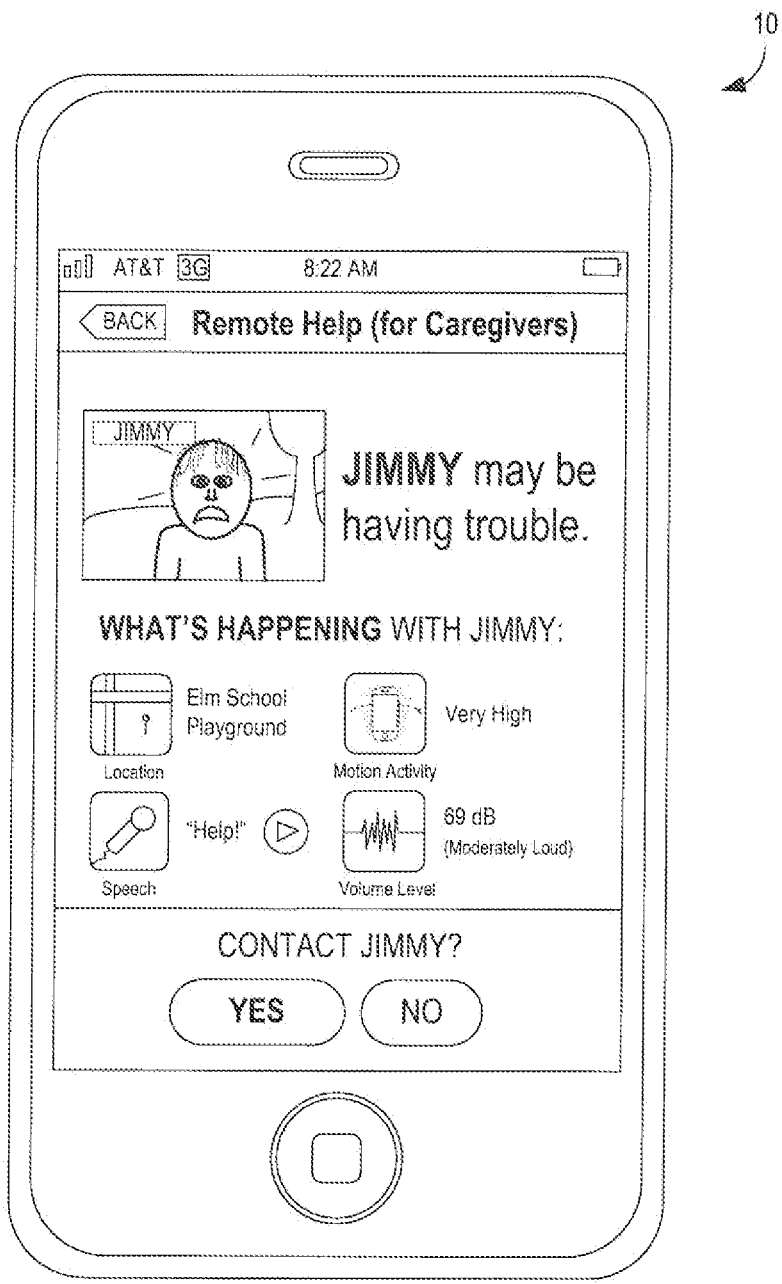
FIG. 22 illustrates a twenty-second screen shot associated with the flow chart of FIG. 5.

FIG. 22 illustrates a screen of a caregiver-specific version of the software. While many such screens and arrangements for each are possible, this particular example demonstrates some of the functionality that may be available. As shown, the caregiver can: (i) receive alerts or updates on the status of a disabled software user (e.g., based on automated help rules as described herein, periodically, or continuously), (ii) view images of the disabled software user (e.g., recently taken by integrated camera 24; e.g., a live, streaming feed from integrated camera 24), (iii) view the disabled user's current geographic location, (iv) view an indication of motion activity occurring in the environment proximate to the disabled user's mobile terminal 10, (v) listen to a recent audio recording in which the disabled user's speech has been captured, (vi) view an indication of the ambient volume level in the environment proximate to the disabled user's mobile terminal 10, and (vii) initiate communications with the co-registered mobile terminal belonging to the disabled user (e.g., place a phone call, text message, etc.). A variety of media may be shared between the two devices in this manner (e.g., the caregiver can review data related to the disabled individual's behavior, environment and body, and can respond by calling the individual, writing a note, or sending back other media including pictures, videos, etc., which may help the disabled individual cope with the current situation).

In some embodiments, a caregiver may use a caregiver-specific version of the software to remotely control a mobile terminal 10 in the possession of a disabled user. For example, after receiving a notification that a child is disoriented in a loud environment, a caregiver responds by: (i) sending a text message informing the child to plug in and wear a peripheral headset, and (ii) sending an instruction such that the child's mobile terminal outputs a soothing piece of classical music stored electronically on the child's mobile terminal. In another example, a caregiver possesses a mobile terminal loaded with a caregiver-specific software application that lets the parent select buttons/options to "Buzz Jimmy's Phone," "Make Jimmy's Phone say 'Hello My Name is Jimmy,'" "Make Jimmy's Phone say 'I have autism, please be patient with me'," etc. In this manner, the caregiver may remotely manipulate voice output software on the mobile terminal 10 to help them communicate.

In some embodiments, bundles or packages featuring multiple copies of the software may comprise copies for multiple caregivers and/or multiple disabled individuals. For example, two parents may each utilize a caregiver-specific version, while their child uses another version (e.g., a "family pack"). In another example, a speech therapist uses a caregiver-specific version, while each of her clients use a version designed to track their speech and provide updates to the therapist, who may "patch in" and help certain clients at certain times. When multiple caregivers are registered in conjunction with a disabled individual, caregivers may periodically "sign-in" and note that they are available or "on duty" through use of the caregiver-specific version of the software. Given the wide array of sensors and technologies described herein, caregivers of all sorts (e.g., parents, teachers, relatives, speech therapists, occupational therapists, physical therapists, nannies or day care service providers, caretakers of elders, paraprofessionals, aides, psychologists, nurses, doctors, spiritual advisors, etc.) may assist disabled users of all sorts (e.g., those with ASD; Down syndrome; cerebral palsy; Fragile X syndrome; ADD/ADHD; cognitive challenges; anxiety stress and panic-related disorders; Alzheimer's disease; Parkinson's disease; dementia; stroke; brain injury; seizure disorders; diabetes; physical impairments; etc.) in such a manner. Moreover, a schedule may be constructed and/or maintained to ensure continuity in monitoring a given disabled user by the various caregivers associated with the given disabled individual. For example, if a certain caregiver that is schedule to be "on call" for a particular disabled user does not respond to a prompt or message, then another caregiver associated with the disabled user may be recruited to maintain the monitoring function during the given period.

The methods described above lend themselves to a database of saved user profiles. An exemplary user profile database is depicted by FIG. 23. Each record of the user profile database may be given a unique identifier (e.g., P-0001). Each record may then store various data in association with the unique identifier. A profile name as entered by a caregiver may be saved (e.g., "Jimmy Smith"). An indication of whether or not the profile is currently loaded for use by the software may also be saved. Within each profile, various user-programmed settings may be stored. For example for each automated help rule that is programmed, the database may store: (i) a first trigger (e.g., an indication of what should initiate automated communications, such as a detected speech part); (ii) a first trigger type (e.g., behavioral, environmental, or biometric); (iii) any sensors or other technologies implicated in detecting the first trigger (e.g., a microphone, GPS technology, a peripheral ring, etc.); (iv) a second trigger, second trigger type, and sensors implicated in detecting the second trigger (if applicable; not shown); (v) a coverage period (e.g., a time and date during which the rule is "in effect"); (vi) a communication medium, or if more than one medium applies, communications media (e.g., phone call, email, text message, blog or Website post, etc.); (vii), the body of the communication (e.g., any text to be included in a text-based communication or included as TTS in a voice communication); (viii), caregiver name(s) (e.g., for any caregivers listed as a recipient of the automated communication), and (ix) contact information for any specified caregivers (e.g., phone numbers, email addresses, instant message handles, etc.). Thus, as software of the present disclosure is programmed, data may be stored, and subsequently accessed to facilitate the execution of process steps shown by the flowchart of FIG. 5. If necessary, such a database may include other fields not shown by FIG. 23 (e.g., to indicate any media attachments, preferences, or other data associated with a rule). The database may be stored locally by mobile terminal 10, or by a central server in communication with the mobile terminal 10.

In addition to the various embodiments disclosed above, various alternate embodiments are also contemplated. These alternate embodiments are not meant to be mutually exclusive with those previously disclosed or with one another. In one such alternate embodiment, a caregiver may configure the software such that automated communications are trigger based only on a schedule. For example, at 4:00 PM, a text message should be sent from a child's mobile terminal to a parent's mobile terminal, informing the parent as to the current geographic location of the child's mobile terminal.

In one embodiment, criteria for triggering automated communications may be inferred and configured automatically by the software based on responses to survey questions. For example, a caregiver (or disabled individual) may answer a series of questions using a mobile terminal 10 or a computer 54. In one embodiment, the survey is conducted as a requisite step when a user first opens the software. For example, a caregiver may complete an "intake" survey or questionnaire about a child with a sensory processing disability, providing information about the child's specific sensory deficits. Such a survey is known in the art as a "Sensory Profile," "Sensory Processing Disorder Survey," or "Sensory Processing Measure Survey," and elements of a prior art survey developed by Winnie Dunn, Ph.D. of the University of Kansas Medical Center may be used for purposes of this disclosure. When completing the survey, caregivers mark "Always," "Frequently," "Occasionally," "Seldom," "Never" in response to various behaviors associated with a child's tactile sensitivity (e.g., "Expresses distress during grooming"), taste/smell sensitivity (e.g., "Limits self to certain food textures/temperatures"), movement sensitivity (e.g., "Becomes anxious or distressed when feet leave the ground"), sensory-seeking behavior (e.g., "Enjoys strange noises/seeks to make noise for noise's sake"), auditory filtering (e.g., "Is distracted or has trouble when there is lots of noise around"), kinetic energy (e.g., "Has a weak grasp"), visual/auditory sensitivity (e.g., "Covers eyes or squints to protect eyes from light"), etc. Criteria for triggering automated communications may then by formed by the software based on responses to the questions; for example, if the caregiver indicates a child is frequently distracted when there is lots of noise around, an automated help rule may be created whereby the caregiver is alerted via text message if the child's mobile terminal 10 detects ambient noise above a threshold decibel level for a period of time. Intake surveys for other disabilities or conditions may be conducted in a similar manner.

In one embodiment, criteria for triggering automated communications may be developed based on continued use of the software. For example, a database may track behavioral, environmental and biometric data related to a disabled user. In one example, if a certain type of behavior is undesirable, an antecedent environmental occurrence may be determined based on the database (e.g., data indicate a child with autism screams and tantrums when near trains or a train station, the train station may be considered an antecedent to the undesirable tantruming behavior). The antecedent may then serve as a criterion for initiating automated communications (e.g., a caregiver is contacted when a child begins to approach a train station, as determined by GPS). Various methods of tracking and associating user behaviors and environmental antecedents are described in Applicant's co-pending provisional patent applications 61/152,907, filed Feb. 16, 2009 and entitled "METHODS FOR RECORDING AND ANALYZING ENVIRONMENTAL AND BEHAVIORAL DATA USING A MOBILE TERMINAL" and 61/227,480, filed Jul. 22, 2009 and entitled "METHOD FOR RECORDING AND ANALYZING ENVIRONMENTAL, BIOLOGICAL AND BEHAVIORAL DATA CONCERNING AUTISM AND OTHER DISABILITIES USING A MOBILE TERMINAL"; these documents are hereby incorporated by reference for all purposes.

In some embodiments, upon the initiation of automated communications, one or more input devices associated with a mobile terminal 10 may be automatically disabled. For example, upon the placement of a phone call from a disabled individual's mobile terminal 10 to a caregiver, the display screen 16 of the mobile terminal may be disabled or locked (e.g., for the duration of the call, or until enabled or unlocked by a physically present caregiver). This may prevent undesirable behavior such as the disabled individual's premature selection of an "End Call" option.

In some embodiments, upon the initiation of automated communications, functionality associated with a mobile terminal 10 may be automatically enabled. For example, upon placing a call, a speakerphone option may automatically be enabled. In other example, upon automatically sending a text message, speaker 14 may output an audio indication that such automated communications have been initiated (e.g., "A text message has been sent to Sandra Brown").

In some embodiments, an automated communication initiated from a mobile terminal 10 may be only partially automated. In one example, a disabled user of mobile terminal 10 may have an option to approve or reject an automated communication before it is sent (e.g., a text message is automatically "typed" by the software on behalf of the user, such that all the user need do is press a button to send the message). In another example, a physically present caregiver must approve an automatically generated communication before it is initiated (e.g., a child's aide at school must key in a four-digit code to approve a message that will be sent to a remote care center).

In some embodiments, a disabled user of the mobile terminal 10 may proactively request help (i.e., without regard for an automated help rule). This may be facilitated in a variety of manners, such that disabled users may bypass many of the normal steps required to seek remote help (e.g., type in a phone number, look up a contact within an electronic address book, etc.). In one example, with the help of a caregiver, a disabled user may program a voice command for calling or sending a prefabricated text or email message to a particular caregiver. In another example, by holding down one or more buttons (e.g., in a sequence, or simultaneously) the disabled user may initiate automated communications (e.g., software is programmed such that by simultaneously holding down two particular buttons for five seconds, a prefabricated text message is automatically sent to a first phone number, a call is placed to a second phone number, and a prefabricated block of text is posted on an online social network). In another example, accelerometer 34 is leveraged such that, after the software is so programmed, a disabled user may simply "shake three times" to initiate communications with one or more particular caregivers. Any series or combination of buttons, commands or inputs may be similarly programmed to initiate an automated communication. In yet another example, a button or icon for proactively initiating communications may be depicted by a touch screen display 16, and to facilitate a disabled user's ability to actuate the button or icon at an appropriate time, the button or icon may change in size based on one or more of: (i) the level of fine motor control demonstrated by a user, (ii) the ambient noise volume as detected by a microphone (e.g. the louder the noise detected, the bigger the button), (iii) the brightness of the environment surrounding the mobile terminal as measured by a light sensor, (iv) an amount of motion activity as detected by a motion sensor and/or accelerometer 34, (iv) biometric data as gleaned from one or more of the sensors described herein (e.g., as heart rate increases, so does the size of the button), (v) speech as uttered by a user and detected by a microphone (e.g., each time the user mentions a particular word, the size of the button grows), and/or (vi) any criterion for initiating a communication with a caregiver disclosed herein.

In one embodiment, as described, a 24-hour remote help service may be made available to the users of software of the present disclosure. The service may provide (e.g., for a monthly fee) access to around-the-clock personnel available to remotely assist disabled users. Such personnel may be trained and work from one or more central offices, or may train and work from their homes using a personal computer. In one embodiment, such personnel may respond to automated communications placed by mobile terminals 10 in conjunction with software of the present disclosure (e.g., as shown by FIG. 20C, an individual may use a personal computer to respond to a plurality of such alerts in parallel or in series). In another embodiment, such personnel may monitor a mobile terminal user in substantially continuous or periodic basis (e.g., using any received automated communications from the mobile terminal users as guidance in helping to triage their attention between multiple active users or unresolved alerts).

Such a 24-hour remote help service may alternately or additionally comprise an Internet-based service for providing data to caregivers. For example, subscribers to the service may be granted access to a password-protected Website for monitoring a particular disabled individual. For example, after logging in during a lunch break while at work, a father can use the Internet service to review the morning's automated communications and any environmental, behavioral or biometric data that may have been captured and uploaded to a server controlled by the service. For example, the father might review a "digest" of his son's speech, vitals, and geographic location over the course of the morning, and conclude that his son appears to be doing mostly well. However, the father might notice a particular series of automated communications, in this example embodied as posts to a Web server maintained by the Internet service, which were triggered by a particular element of speech the father had been hoping his son would soon improve upon (e.g., "baby talk" that the son has yet to outgrow, a mispronunciation of a word, inappropriate use of a word in context). The father might then initiate contact with the child's speech therapist to address the issue (e.g., as part of the subscription, the therapist is also given access to the Website, allowing the father to "flag" the audio files of the recorded speech along with a note to the therapist expressing his desire to "please work on this").

In one embodiment, the mobile terminal 10 may initiate an automated communication to all "on call" parties within a certain geographical proximity of the disabled user's device. For example, parents of autistic children may belong to an organization that maintains a database of similarly situated parents. When the mobile terminals 10 of such registered parents are determined to be within a certain geographical proximity of a disabled user's mobile terminal 10, and it is determined that the disabled user may need help, the geographically proximate parents may be notified. In this way, the community of caregivers who understand and may be particularly sympathetic to particular afflictions may be notified if someone with the affliction (e.g., autism) needs help. For example, a message to a participating caregiver may read, "An autistic teenager at the Burger King on Bridgeport Avenue needs your help. Press 'Yes' to indicate that you can be there within 10 minutes. Thank you for being part of the Autism Everyday Help Network." Caregivers may affirmatively respond to a request for assistance sent on behalf of a disabled individual, such that the request is no longer considering pending.

In still another embodiment, some of the processing may be removed from the mobile terminal 10 and handled by a remotely positioned control system. That is, the mobile terminal 10 merely sends periodic signals including the data from the sensors (camera 24, microphone 26, accelerometer 34, peripherals 44, and/or peripheral devices 58 or the like) to the remotely positioned control system. The remotely positioned control system may then compare the data to a profile created on computer 54 and transmitted to the remotely positioned control system to determine if the criterion meets or exceeds any threshold and may initiate communications to a remote caregiver according to the rules of the profile. As another variation, the mobile terminal 10 initiates contact to the remotely positioned control system based on the locally stored profile, but the remotely positioned control system determines which remote caregiver should be contacted. In short, the processing and decision making may be distributed as desired or practical.

RULES OF INTERPRETATION & GENERAL DEFINITIONS

Numerous embodiments are described in this disclosure, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this disclosure) nor the Abstract (set forth at the end of this disclosure) is to be taken as limiting in any way as the scope of the disclosed invention(s).

The term "product" means any machine, manufacture and/or composition of matter as contemplated by 35 U.S.C. §101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device or article (whether or not they cooperate) may alternatively be used in place of the single device or article that is described. Accordingly, the functionality that is described as being possessed by a device may alternatively be possessed by more than one device or article (whether or not they cooperate).

Similarly, where more than one device or article is described herein (whether or not they cooperate), a single device or article may alternatively be used in place of the more than one device or article that is described. For example, a plurality of computer-based devices may be substituted with a single computer-based device. Accordingly, the various functionality that is described as being possessed by more than one device or article may alternatively be possessed by a single device or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present disclosure. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, LDP, rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as standard definition (SDTV), enhanced definition (EDTV), high definition (HD), or the like. The information may likewise be static, in which case, painted glass may be used to form the display. Note that static information may be presented on a display capable of displaying dynamic information if desired.

The present disclosure frequently refers to a "control system". A control system, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, CPU devices, computing devices, microcontrollers, digital signal processors, or like devices. Exemplary processors are the INTEL PENTIUM or AMD ATHLON processors.

The term "computer-readable medium" refers to any medium that participates in providing data (e.g., instructions) that may be read by a computer, a processor or a like device. Such a medium may take many forms, including but not limited to, non-volatile media, volatile media, and transmission media. Non-volatile media include, for example, optical or magnetic disks and other persistent memory. Volatile media include DRAM, which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during RF and IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present disclosure.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, Local Area Network (LAN), Wide Area Network (WAN), or Ethernet (or IEEE 802.3), Token Ring, or via any appropriate communications means or combination of communications means. Exemplary protocols include but are not limited to: BLUETOOTH™, TDMA, CDMA, GSM, EDGE, GPRS, WCDMA, AMPS, D-AMPS, IEEE 802.11 (WI-FI), IEEE 802.3, TCP/IP, or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cellular networks, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

The present disclosure provides, to one of ordinary skill in the art, an enabling description of several embodiments and/or inventions. Some of these embodiments and/or inventions may not be claimed in the present disclosure, but may nevertheless be claimed in one or more continuing applications that claim the benefit of priority of the present disclosure.

What is claimed is:

1. A non-transitory computer readable medium comprising software with instructions for a telephonically enabled mobile terminal to:
   store in memory of the mobile terminal a profile for a user, the profile comprising:
      criteria for facilitating communications between the mobile terminal, a first remote individual, and a second remote individual;
   determine whether a criterion of the criteria has been met;
   initiate a first alert to the first remote individual without intervention by the user when one of the criteria has been met, wherein the first remote individual receives a first notification via a first alert type; and
   initiate a second alert to the second remote individual without intervention by the user when the one of the criteria has been met, wherein the second remote individual receives a second notification via a second alert type.

2. The computer readable medium of claim 1 wherein an alert type used for initiated first and second alerts comprises:
   a modality, which is selected from the group consisting of: a phone call, a text message, an instant message, an email, a post to a public website, and a post to a private online server; and
   a media preference, which specifies a format, text, audio, and/or video associated with a communication.

3. The computer readable medium of claim 1 wherein the software further comprises instructions to use at least one sensor of the mobile terminal to detect conditions related to the criterion.

4. The computer readable medium of claim 1 wherein the software further comprises instructions to use a remotely positioned sensor communicatively coupled to the mobile terminal to detect conditions related to the criterion.

5. The computer readable medium of claim 4 wherein the software further comprises instructions to compare an output of the remotely positioned sensor to a predefined threshold.

6. The computer readable medium of claim 1 wherein the instructions to determine whether the criterion has been met comprise instructions to evaluate a current position of the mobile terminal relative to a predefined geographical zone.

7. The computer readable medium of claim 6 further comprising instructions to poll a GPS service to determine the current position of the mobile terminal.

8. The computer readable medium of claim 6 wherein the predefined geographical zone is defined by selecting a point on a map and then specifying a radius in association with the point.

9. The computer readable medium of claim 6 wherein a predefined geographical zone is associated with a text label specified by the user.

10. The computer readable medium of claim 1 wherein the profile for the user stores baseline geographic data measured in association with the user.

11. The computer readable medium of claim 9 wherein the determination of whether a criterion of the criteria has been met is based at least in part on baseline geographic data.

12. The computer readable medium of claim 1 wherein the alert comprises a link to additional information about the user.

13. A method comprising:
   storing in memory of a telephonically enabled mobile terminal a profile for a user, the profile comprising:
      criteria for facilitating communications between the mobile terminal, a first remote individual, and a second remote individual;
   determining whether a criterion of the criteria has been met;
   initiating an alert to the first remote individual without intervention by the user when one of the criteria has been met, wherein the first remote individual receives a notification via a first alert type; and
   initiating an alert to the second remote individual without intervention by the user when one of the criteria has been met, wherein the second remote individual receives a notification via a second alert type.

14. A method comprising:
   receiving first input from a user regarding a criterion;
   receiving second input from the user regarding a plurality of remote individuals, wherein the second input specifies means for contacting each remote individual of the plurality of remote individuals;
   receiving third input from one or more sensors associated with a mobile terminal;
   comparing the third input from the one or more sensors to the criterion;
   based at least in part on the comparing, determining that an event has occurred;
   causing a signal to be sent to a first remote individual without intervention by the user in response to the occurrence of the event, wherein the signal to be sent to the first remote individual is associated with a first format; and
   causing a signal to be sent to a second remote individual without intervention by the user in response to the occurrence of the event, wherein the signal to be sent to the second remote individual is associated with a second format.

15. The method of claim 14 wherein receiving the first input comprises receiving the first input through a user interface on a mobile terminal.

16. The method of claim 14 wherein receiving the first input comprises receiving the first input through a user interface on a computer and transmitting it to a mobile terminal.

17. The method of claim 14 wherein receiving the third input comprises receiving the third input from a GPS service to determine a current location of the mobile terminal.

18. The method of claim 17 wherein comparing the third input from the GPS service comprises determining if the mobile terminal is within a predefined zone.

19. The method of claim 14 wherein the event comprises a change in geographic location.

20. A method comprising:
   storing a first criterion for facilitating communications between a user of a mobile terminal and a first remote individual, wherein the first criterion is associated with a first alert style;
   storing a second criterion for facilitating communications between the user of the mobile terminal and a second remote individual, wherein the second criterion is associated with a second alert style;
   determining whether the first criterion or the second criterion has been satisfied; and
   establishing a communication to either the first remote individual or the second remote individual based on the result of the determining step.

* * * * *